(12) United States Patent
Skubic et al.

(10) Patent No.: US 10,188,295 B2
(45) Date of Patent: Jan. 29, 2019

(54) INTEGRATED SENSOR NETWORK METHODS AND SYSTEMS

(75) Inventors: Marjorie Skubic, Columbia, MO (US); Marilyn J. Rantz, Rocheport, MO (US); Mihail Popescu, Columbia, MO (US); Shuang Wang, Irvine, CA (US); Isaac J. Sledge, Columbia, MO (US); Rainer Dane A. Guevara, Columbia, MO (US); Elena Florea, Columbia, MO (US); James M. Keller, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 1235 days.

(21) Appl. No.: 12/791,628

(22) Filed: Jun. 1, 2010

(65) Prior Publication Data
US 2010/0302043 A1 Dec. 2, 2010

Related U.S. Application Data

(60) Provisional application No. 61/217,623, filed on Jun. 1, 2009.

(51) Int. Cl.
*A61B 5/00* (2006.01)
*A61B 5/0205* (2006.01)
(Continued)

(52) U.S. Cl.
CPC ............ *A61B 5/002* (2013.01); *A61B 5/0022* (2013.01); *A61B 5/0205* (2013.01);
(Continued)

(58) Field of Classification Search
None
See application file for complete search history.

(56) References Cited

U.S. PATENT DOCUMENTS 5,309,921 A * 5/1994 Kisner et al. ............... 600/532
6,002,994 A * 12/1999 Lane et al. .................. 702/188
(Continued)

OTHER PUBLICATIONS

Office action for U.S. Appl. No. 12/791,496 dated Apr. 26, 2013.
(Continued)

*Primary Examiner* — Brian A Zimmerman
*Assistant Examiner* — Kevin Lau
(74) *Attorney, Agent, or Firm* — Thompson Coburn LLP

(57) ABSTRACT

Methods and systems for an integrated sensor network are described. In one embodiment, sensor data may be accessed from a plurality of motion sensors and a bed sensor deployed in a living unit for a first time period. An activity pattern for the first time period may be identified based on at least a portion of sensor data associated with the first time period. The activity pattern may represent a physical and cognitive health condition of a person residing in the living unit. Additional sensor data may be accessed from the motion sensors and the bed sensor deployed for a second time period. A determination of whether a deviation of the activity pattern of the first time period has occurred for the second time period may be performed. An alert may be generated based on a determination that the derivation has occurred. In some embodiments, user feedback is captured on the significance of the alerts, and the alert method is customized based on this feedback. Additional methods and systems are disclosed.

35 Claims, 27 Drawing Sheets

(51) Int. Cl.

| | |
|---|---|
| *A61B 5/11* | (2006.01) |
| *G08B 21/04* | (2006.01) |
| *G16H 50/20* | (2018.01) |
| *G06F 19/00* | (2018.01) |
| *A61B 5/021* | (2006.01) |
| *A61B 5/024* | (2006.01) |
| *A61B 5/08* | (2006.01) |
| *G16H 15/00* | (2018.01) |

(52) U.S. Cl.
CPC .......... *A61B 5/1113* (2013.01); *A61B 5/1118* (2013.01); *G06F 19/00* (2013.01); *G08B 21/0423* (2013.01); *G16H 50/20* (2018.01); *A61B 5/021* (2013.01); *A61B 5/024* (2013.01); *A61B 5/0816* (2013.01); *A61B 5/7264* (2013.01); *A61B 2503/08* (2013.01); *A61B 2505/07* (2013.01); *A61B 2560/0242* (2013.01); *G16H 15/00* (2018.01)

(56) References Cited

U.S. PATENT DOCUMENTS

| | | | |
|---|---|---|---|
| 6,915,008 | B2 | 7/2005 | Barman et al. |
| 7,420,472 | B2 | 9/2008 | Tran |
| 7,843,351 | B2* | 11/2010 | Bourne et al. ............. 340/573.7 |
| 2003/0058111 | A1 | 3/2003 | Lee et al. |
| 2003/0059081 | A1* | 3/2003 | Trajkovic ...................... 382/100 |
| 2003/0085992 | A1 | 5/2003 | Arpa et al. |
| 2003/0189485 | A1* | 10/2003 | Smith ................ G08B 21/0423 340/540 |
| 2004/0030531 | A1 | 2/2004 | Miller et al. |
| 2004/0119716 | A1 | 6/2004 | Park et al. |
| 2004/0228503 | A1 | 11/2004 | Cutler |
| 2005/0088515 | A1 | 4/2005 | Geng |
| 2005/0094879 | A1 | 5/2005 | Harville |
| 2006/0055543 | A1* | 3/2006 | Ganesh et al. ............. 340/573.1 |
| 2007/0003146 | A1 | 1/2007 | Ko et al. |
| 2007/0152837 | A1* | 7/2007 | Bischoff et al. ........... 340/573.1 |
| 2007/0263900 | A1 | 11/2007 | Medasani et al. |
| 2008/0117060 | A1* | 5/2008 | Cuddihy ............. G06F 19/3418 340/573.1 |
| 2009/0079559 | A1 | 3/2009 | Dishongh et al. |
| 2009/0079813 | A1* | 3/2009 | Hildreth ...................... 348/14.03 |
| 2009/0089089 | A1 | 4/2009 | Jang et al. |
| 2010/0330543 | A1* | 12/2010 | Black ...................... G09B 7/02 434/236 |

OTHER PUBLICATIONS

Martin, et al., "Gait Initiation in Community-Dwelling Adults with Parkinson Disease: Comparison with Older and Younger Adults without the Disease," Physical Therapy, Jun. 2002, vol. 82, No. 6 pp. 566-577 from www.physther.org.

Wall, et al., "The timed get-up-and-go test revisited: Measurement of the component tasks," Department of Vetrans Affairs, Journal of Rehabilitation Research and Development vol. 37 No. 1, Jan./Feb. 2000, pp. 109-114.

Yaguchi, et al., "Arbitrary Viewpoint Video Synthesis from Multiple Uncalibrated Cameras," IEEE Transactions on Systems, Man, and Cybernetics—Part B: Cybernetics, vol. 34. No. 1, Feb. 2, pp. 430-439.

Andersen, "Recognizing Falls from Silhouettes", Proceedings of the 28th IEEE, EMBS Annual International Conference, New York City, USA Aug. 30-Sep. 3, 2006.

Davis et al., "Toward 3-D Gesture Recognition," Research supported by the National Science Foundation grants CDA-9200369, IRI-9122006 and IRI-9220768.

Final Office action for U.S. Appl. No. 12/791,496 dated Nov. 5, 2013.

Harvey, N. et al, Speedup of Fuzzy Logic through Stream Processing on Graphics Processing Units, In Proceedings: IEEE Congress on Evolutionary Computation, 2008, pp. 3809-3814.

Sledge, I.J. et al, Emergent Trend Detection in Diurnal Activity, 30th Annual International IEEE EMBS Conference, Vancouver, British Columbia, Canada, Aug. 20-24, 2008, pp. 3815-3818.

* cited by examiner

INTEGRATED SENSOR NETWORK METHODS AND SYSTEMS

CROSS-REFERENCE TO RELATED APPLICATIONS

This application claims the benefit of United States Provisional Patent Application entitled "Monitoring System for Eldercare", Ser. No. 61/217,623, filed 1 Jun. 2009, the entire contents of which is herein incorporated by reference.

GRANT STATEMENT

This invention was made with government support under Grant No. IIS-0428420 and, Grant No. 90AM3013 awarded by the U.S. Administration on Aging, and Grant No. 1R21NR011197-01 awarded by the National Institute of Health. The government has certain rights in the invention.

FIELD

This application relates to methods and systems for sensor networks, and more specifically to methods and systems for integrated sensor networks.

BACKGROUND

Countries on multiple continents are experiencing an aging population. The number of older adults is growing dramatically. With this demographic shift, there is a desire to keep older adults healthy, functionally able, and living independently, in part because this provides a better quality of life, and in part because the aging population will stress current facilities and resources designed to care for elders. Challenges exist in keeping people healthy and functionally able as they age.

DETAILED DESCRIPTION

Example methods and systems for an integrated sensor network are described. In the following description, for purposes of explanation, numerous specific details are set forth in order to provide a thorough understanding of example embodiments. It will be evident, however, to one of ordinary skill in the art that embodiments of the invention may be practiced without these specific details.

Most adults would prefer to remain as active as possible and to live independently in unrestricted environments as they age. However, because chronic illness and declining health affect most people as they get older, placement in more restricted housing environments like assisted living or nursing homes is fairly common. The reason this sort of placement occurs is because health assessments and medical care have traditionally required face to face meetings.

One alternative consideration for monitoring older adults includes the use of smart sensor technologies as part of an integrated sensor network that detects activity levels around them and electronically sends the activity data to a central repository. Through web technologies, data can be accessed and viewed by health care providers, families or others interested in the health of the older person being monitored.

The integrated sensor network includes simple motion sensors, a stove sensor, video sensors, and a bed sensor that captures sleep restlessness and pulse and respiration levels. Patterns in the sensor data may represent physical and cognitive health conditions. Recognition may be performed when activity patterns begin to deviate from the norm. Performing the recognition may enable early detection of potential problems that may lead to serious health events if left unattended.

Figure 1:
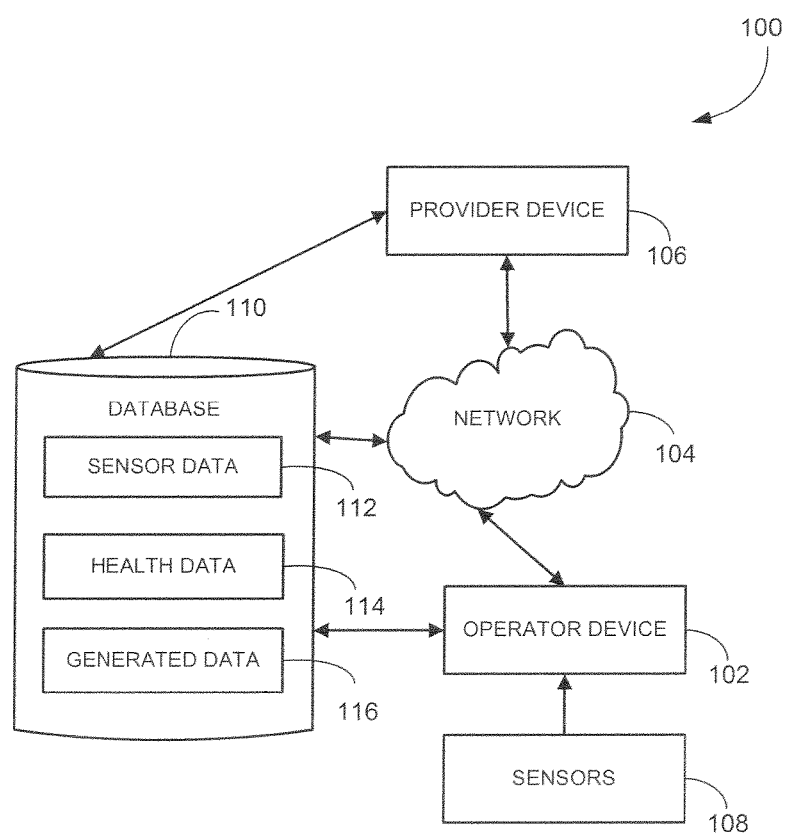
FIGS. 1 and 2 are block diagrams of example systems, according to example embodiments.

FIG. 1 illustrates an example system 100 in which an integrated sensor network may be used. The system 100 is an example platform in which one or more embodiments of the methods may be used. However, the integrated sensor network may also be used on other platforms.

An operator may use the integrated sensor network by using the operator device 102. The integrated sensor network may be used by a person residing in a living unit. The operator device 102 may be located in the living unit, outside of the living unit but in a living unit community, or a location outside of the living unit community. Examples of operators include clinicians, researchers, and the like.

The operator may use the operator device 102 as a stand-alone device to use the integrated sensor network, or may use the operator device 102 in combination with a provider device 106 available over a network 104. In some embodiments, the provider device 106 is also under the control of the operator but at a location outside of the living unit community.

The operator device 102 may be in a client-server relationship with the provider device 106, a peer-to-peer relationship with the provider device 106, or in a different type of relationship with the provider device 106. In one embodiment, the client-server relationship may include a thin client on the operator device 102. In another embodiment, the client-server relationship may include a thick client on the operator device 102.

The network 104 over which the operator device 102 and the provider device 106 may communicate include, by way of example, a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

In one embodiment, the provider device 106 is a single device. In one embodiment, the provider device 106 may include multiple computer systems. For example, the provider device 106 may include multiple computer systems in a cloud computing configuration.

Multiple sensors 108 forming a sensor network are included in the system 100 to obtain sensor data 112. Examples of sensors 108 include motion sensors, a bed sensor, and a stove sensor. In general, the multiple sensors 108 are passive, nonwearable sensors.

The operator device 102, the provider device 106, or both may communicate with a database 110. The database 110 may contain sensor data 112, health data 114, and generated data 116.

The sensor data 112 may be received from the sensors 108 or otherwise accessed (e.g., indirectly accessed by the provider 106 from the operator device 102). The health data 114 includes health related information about people. In general, the health data 114 is for the people associated with a particular doctor, healthcare organization, and/or living unit community. The generated data 116 includes information received and stored based on use of the integrated network.

Figure 2:
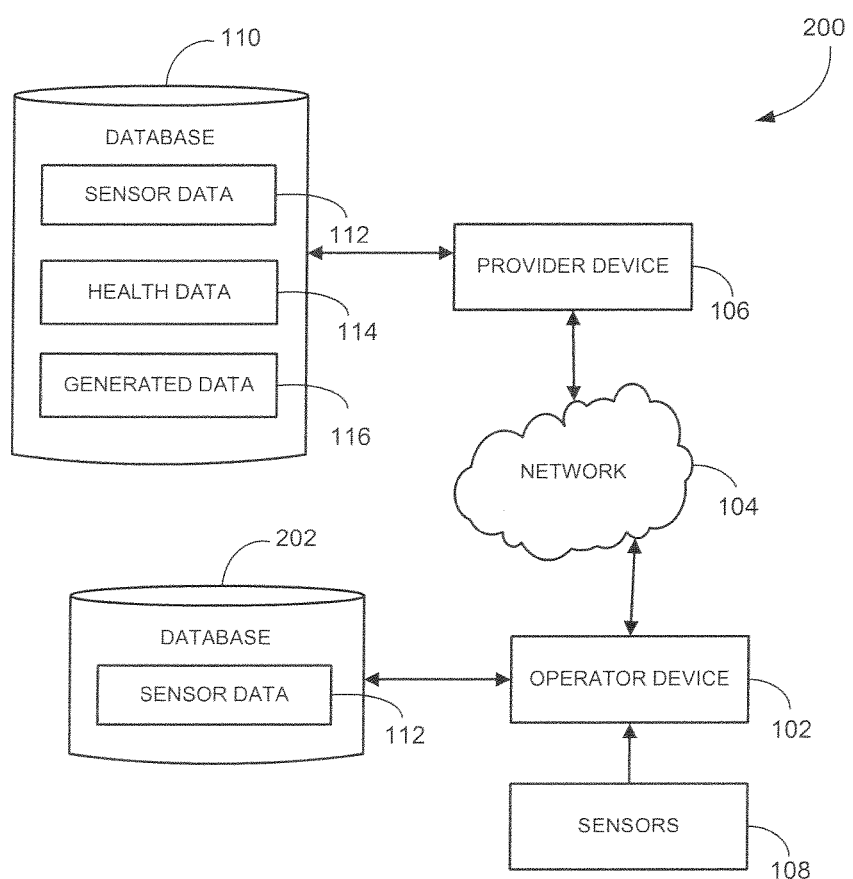

FIG. 2 illustrates an example system 200, according to an example embodiment. The system 200 is a specific example of the system 100. As shown in the system 200, the sensor data 112 is received by the operator device 102 from the sensors 108 and stored in a database 202. The operator device 102 is a logging device that simply collects the sensor data 112 and does not regularly receive input from the person, the operator, or otherwise.

The operator device 102 transmits the sensor data 112 to the provider device 106 for storage in the database 110 on a regular basis. The sensor data 112 may be transmitted, hourly, daily, weekly, or at other greater or lesser time increments. The provider device 106 of the system 200 may include multiple provider devices including client provider devices and server provider devices. The operator may communicate with a server provider device through a user interface or otherwise.

Figure 3:
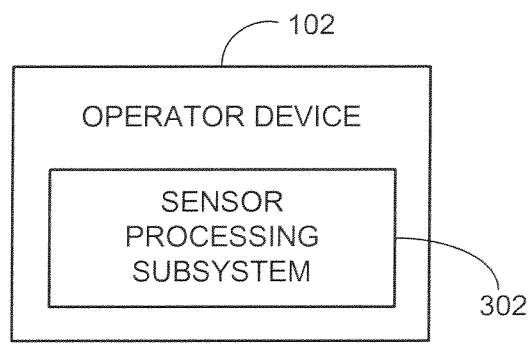
FIG. 3 is a block diagram of an example operator device that may be deployed within the system of FIG. 1, according to an example embodiment.

FIG. 3 illustrates an example operator device 102 that may be deployed in the system 100 (see FIG. 1), or otherwise deployed in another system. The operator device 102 is shown to include a signal processing subsystem 302 to enable use of the integrated sensor network.

Figure 4:
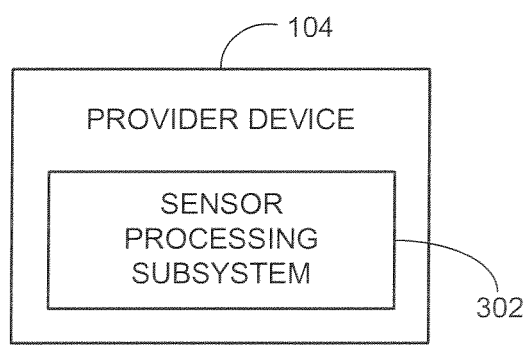
FIG. 4 is a block diagram of an example provider device that may be deployed within the system of FIG. 1, according to an example embodiment.

FIG. 4 illustrates an example provider device 106 that may be deployed in the system 100 (see FIG. 1), or otherwise deployed in another system. The provider device 106 is shown to include a signal processing subsystem 302 to enable use of the integrated sensor network.

In one embodiment, the functionality that enables use of the integrated sensor network voxel model resides solely on the sensor processing subsystem 302 deployed in the operator device 102. In another embodiment, the functionality resides solely on the sensor processing subsystem 302 deployed in the provider device 106. In another embodiment, the functionality is partially performed on the sensor processing subsystem 302 deployed in the operator device 102 and partially performed on the sensor processing subsystem 302 deployed in the provider device 106. The functionality may otherwise be distributed among the operator device 102, the provider device 106, or another device.

Figure 5:
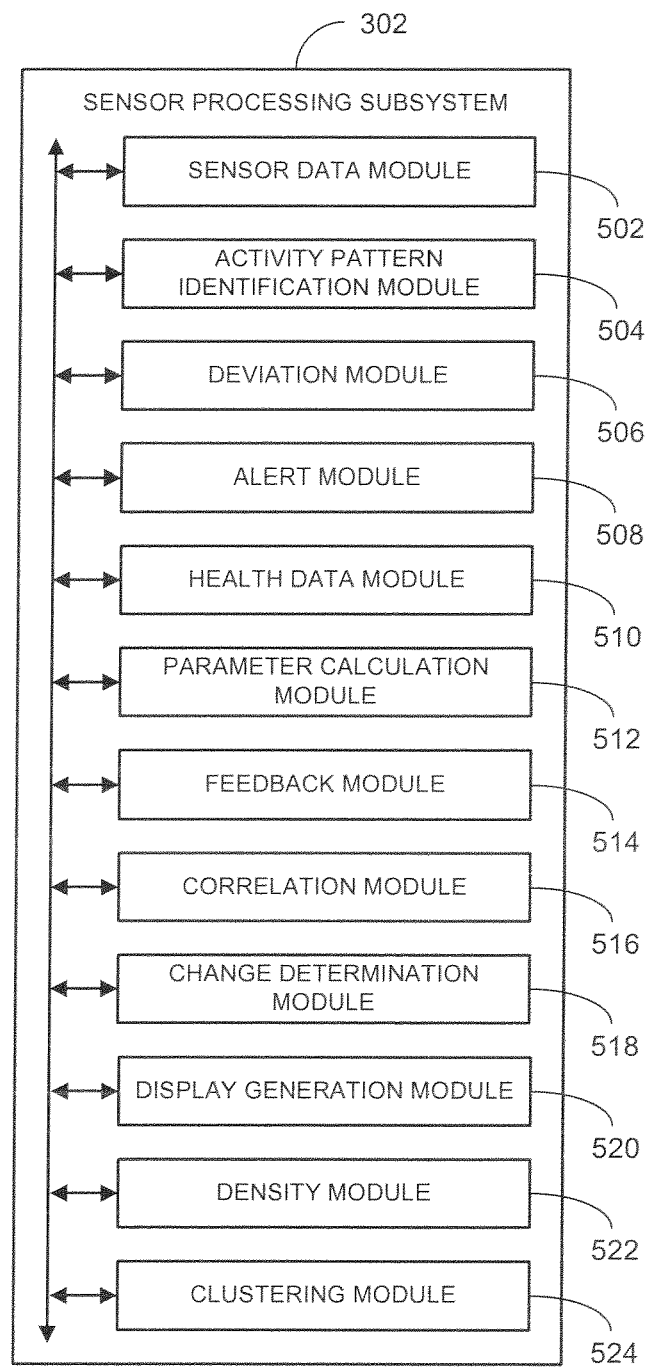
FIG. 5 is a block diagram of an example sensor processing subsystem that may be deployed within the operator device of FIG. 3 or the provider device of FIG. 4, according to an example embodiment.

FIG. 5 illustrates an example sensor processing subsystem 302 that may be deployed in the operator device 102, the provider device 106, or otherwise deployed in another system. One or more modules are included in the sensor processing subsystem 302 to process the sensor data 112. The modules of the signal processing subsystem 302 that may be included are a sensor data module 502, an activity pattern identification module 504, a deviation module 506, an alert module 508, a health data module 510, a parameter calculation module 512, a feedback module 514, a correlation module 516, a change determination module 518, a display generation module 520, a density module 522, and/or a clustering module 524. Other modules may also be included. In various embodiments, the modules may be distributed so that some of the modules may be deployed in the operator device 102 and some of the modules may be deployed in the provider device 106. In one particular embodiment, the signal processing subsystem 302 includes a processor, memory coupled to the processor, and a number of the aforementioned modules deployed in the memory and executed by the processor.

The sensor data module 502 accesses the sensor data 112. The sensor data 112 may be associated with motion sensors deployed in a living unit, a bed sensor deployed in a living unit, a stove sensor deployed in the living unit, other environmentally-mounted, nonwearable sensors, or combinations thereof. In general, the sensors 108 are passive, non-wearable sensors. The sensor data 112 accessed by the sensor data module 502 may be for a time period.

In some embodiments, the living unit is an apartment. In other embodiments, the living unit is a house.

The activity pattern identification module 504 identifies an activity pattern for the time period based on at least a portion of the sensor data 112 accessed by the sensor data module 502. In some embodiments, the activity pattern represents a physical and cognitive health condition of a person living in the living unit. In one embodiment, activity pattern includes a single feature. In another embodiment, the activity pattern includes multiple features.

In some embodiments, the sensor data module 502 identifies at least a portion of the sensor data 112 associated with the time period as being associated with the person. Identification of the activity pattern for the first time period is based on at least the portion of the sensor data 112 associated with the first time period associated with the person.

In some embodiments, the sensor data module 502 accesses additional sensor data 112 for an additional time period that occurs after a first time period. The deviation module 506 may then determine whether a deviation of the activity pattern of the first time period has occurred for the additional time period. The alert module 508 generates an alert based on a determination that the derivation has occurred.

In some embodiments, the alert module 508 transmits the alert. In some embodiments, the alert module 508 stores the alert. The alert module 508 may otherwise use or process the alert.

In some embodiments, event listeners (the observers) register with an event provider associated with the alert module 508 to be notified of sensor events (the changes). The event provider may support a filtering operation. That is, a template for the sensor events can be specified so that event listeners are only notified if a sensor event matches the template.

The alert module 508 provides a cohesive yet flexible mechanism for incorporating different types of alert conditions. State machines may be used by alert providers to model alert specifications. As sensor events are observed, an alert model associated with the alert module 508 may transition to a new state and, if warranted, will generate an alert condition.

Timers may be included for state transitions. The state machine generalization supports simple one-sensor alerts as well as alerts that involve more complex interactions among multiple sensors. The alert module 508 easily accepts inputs from multiple sources. Sensor events may be replayed from the database 110 through the use of the generated data 116, to facilitate testing of alert algorithms. Alerts may be sent to different output streams, including a pager system for immediate alerts as well as emailed alerts for daily summaries.

In some embodiments, the activity pattern identification module 504 identifies the activity pattern for the second time period based on access of the additional sensor data 112 associated with the second time period. The determination of whether the deviation has occurred by the deviation module 506 may then include determining whether the deviation of the activity pattern of the second time period from the activity pattern of the first time period exceeds a threshold.

In some embodiments, the health data module 510 analyzes health data associated with the person. Generation of the alert by the alert module 508 may be based on when the activity pattern of the second time period from the activity pattern of the first time period exceeds the threshold and analysis of the health data 114.

In some embodiments, the parameter calculation module 512 calculates statistical parameters of at least a portion of the sensor data 112 for the time period. A determination of whether the deviation has occurred by the deviation module 506 may then include determining whether at least a portion of the additional sensor data 112 for the additional time period is outside of a threshold based on the statistical parameters.

The alert generated by the alert module 508 may be a hits-based alert. In one embodiment, the activity pattern for the time period is based on total number of sensor hits of a sensor 108 during a day of the time period.

The alert generated by the alert module 508 may be a time-based alert. In one embodiment, the activity pattern for the time period is based on total time that the sensor 108 fired during a particular day of the time period.

In some embodiments, the alert module 508 transmits the alert including a link to a web interface. In one embodiment, the web interface includes the sensor data 112 of the second time period in the context of the sensor data 112 of the first time period.

The feedback module 514 may be deployed in the sensor processing subsystem 302 to receive and process feedback, requests, selections, or the like.

In some embodiments, the feedback module 514 receives a feedback response to the alert. The feedback response includes feedback regarding clinical relevance of the alert. The feedback module 514 may then take action based on receipt of the feedback response.

In one embodiment, the action includes adjusting the threshold based on the receipt of the feedback response. In one embodiment, the action includes recording ignored indicia for the person based on the receipt of the feedback response. The ignored indicia may be associated with a feature of the alert.

In some embodiments, the sensor processing subsystem 302 includes the correlation module 516 and the change determination module 518 to predict changes in a health condition. The health condition may be a physical condition, a mental condition, or a physical and a mental condition. In one embodiment, the health condition is pulse pressure. Pulse pressure may be the difference between systolic blood pressure (SBP) and the diastolic blood pressure (DBP).

By way of example, the sensor data module 502 accesses the sensor data 112 associated with a person and the health module data module 510 accessing the health data 114 of the person for a first time period. The correlation module 516 then correlates the health data to at least a portion of the sensor data 112 for the first time period. The sensor data module 502 accesses additional sensor data 112 for a second time period.

The changer determination module 518 then determines whether a change in a health condition of the person has occurred based on the additional sensor data 112 and correlation of the health condition data to at least the portion of the sensor data 112 for the first time period. The alert module 508 may generate an alert when a determination is made that the change in the health condition has occurred.

The display generation module 520 generates a display. In some embodiments, the alert module 508 generates the alert and the display generation module 520 generates a display based the alert.

In some embodiments, the sensor data module 502 accesses the sensor data 112 and the display generation module 520 generates a display based on the sensor data 112. In one embodiment, the sensor data 112 is grouped on the display based on multiple categories. The categories may include, by way of example, motion, pulse, breathing, and bed restlessness.

In some embodiments, the feedback module 514 receives a selection of a person and a date range. The sensor data module 502 may then access the sensor data 112 based on receipt of the selection.

A user may interface with the sensor processing subsystem 302 to zoom in or zoom out on the display. In some embodiments, the feedback module 514 receives a time interval modification request. The display generation module 520 may then generate a display based on access of the sensor data 112 associated with the time period and receipt of the time interval modification request.

In some embodiments, the feedback module 514 receives a time increment modification request. The display generation module 520 may then generate the display based on access of the sensor data 112 associated with the time period and receipt of the time increment modification request.

The density module 522 determines an away-from-home time period for a person associated with the living unit during the time period. The generation of the display by the display generation module 520 then generates the display based on access of the sensor data 112 and a determination of the away-from-home time period.

In some embodiments, a determination of the away-from home time period by the density module 522 includes analyzing the sensor data 112 to determine whether a living unit departure sensor sequence and a living unit return sensor sequence has occurred and calculating a time difference between occurrence of the living unit departure sensor sequence and occurrence of the living unit return sensor sequence.

In one embodiment, analyzing the sensor data 112 includes applying fuzzy logic to at least a portion of the sensor data 112 to determine whether a living unit departure sensor sequence and a living unit return sensor sequence has occurred.

In some embodiments, the density module 522 computes a number of motion sensor hits for multiple hours. A sensor hit is associated with a motion sensor. The density module

522 may then calculate density for the multiple hours. The generation of the display by the display generation module 520 may then be based on calculation of the density.

In one embodiment, the display generation module 520 selects color mappings and then generates the display based on the selection of color mappings. In general, a color mapping has a color based on the density and is associated with a position on a display based on the hour and day.

Dis-similarity between density maps may be computed by use of the density module 522. In some embodiments, the density module 522 accesses a first density map and a second density map, the first density map having a first color mappings, the second density map having a second color mappings, computes a dis-similarity between the first density map and the second density map based on a textual feature of the first density map and the second density map, and generates a computational result based on computing the dis-similarity. Textual features may include, by way of example, spatial, frequency, and perceptual properties. The display generation module 520 may then generate a display based on computation of the dis-similarity. The density module 520 may transmit a notification based on computation of the dis-similarity, storing the computational result, or both.

Clustering may be performed by the clustering module 524 to analyze the sensor data 112 based on clusters. In some embodiments, the clustering module 524 generates feature clusters for a time period. A feature cluster is associated with multiple feature vectors, wherein a feature vector is associated with the sensor data 112 from at least some of motion sensors and/or a bed sensor. The sensor data module 502 accesses additional sensor data 112 associated a feature for a different time period. The clustering module 524 may then determine whether the additional sensor data 112 falls within the feature clusters or belongs in a new cluster.

Based on a result of the determination, the clustering module 524 generates a notification. The notification may be a cluster addition notification based on a determination that the additional sensor data 112 falls within the feature clusters. The notification may be a new cluster notification based on a determination that the additional sensor data 112 belongs in the new cluster.

Figure 6:
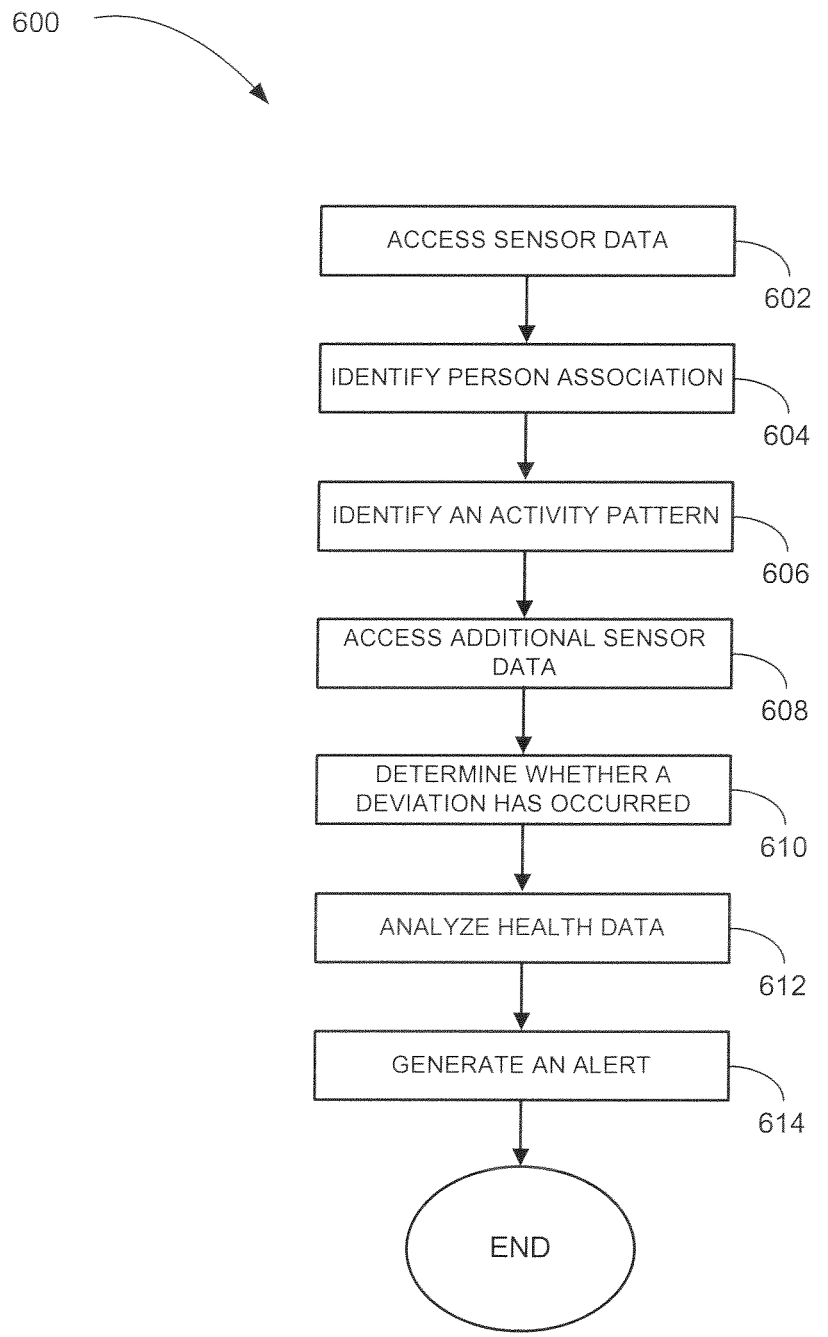
FIGS. 6-8 are block diagrams of flowcharts illustrating methods for sensor processing, according to example embodiments.

FIG. 6 illustrates a method 600 for sensor processing according to an example embodiment. The method 600 may be performed by the operator device 102 or the processor device 106 of the system 100 (see FIG. 1), or may be otherwise performed.

At block 602, the sensor data 112 is accessed from the motion sensors and the bed sensor deployed in a living unit for a first time period. In general, the deployed sensors are passive, non-wearable sensors.

At least a portion of the sensor data 112 associated with the first time period may be identified as being associated with the person at block 604.

An activity pattern is identified for the first time period at block 606 based on at least a portion of sensor data 112 associated with the first time period. In one embodiment, the activity pattern represents a physical and cognitive health condition of a person residing in the living unit. In some embodiments, identification of the activity pattern for the first time period is based on at least the portion of sensor data 112 associated with the first time period associated with the person.

At block 608, additional sensor data 112 is accessed from the motion sensors and the bed sensor deployed in the living unit for a second time period. The second time period occurs after the first time period. In some embodiments, the first period of time has a same time duration as the second period of time.

In one embodiment, the first time period is for a period of fourteen consecutive days and the second time period is for a period of a single day. Different periods of time may be used for the first time period and the second time period.

In some embodiments, the operations performed at block 602 including accessing the sensor data 112 from a stove sensor deployed in the living unit and the operations performed at block 608 include accessing the additional sensor data 112 from the stove sensor deployed in the living unit.

A determination of whether a deviation of the activity pattern of the first time period has occurred for the second time period is performed at block 610. In some embodiments, the activity pattern includes multiple features and the deviation is associated with a feature of the multiple features.

In some embodiments, the activity pattern for the second time period is identified based on access of the additional sensor data 112 associated with the second time period. The determination performed at block 610 may then include determining whether the deviation of the activity pattern of the second time period from the activity pattern of the first time period exceeds a threshold.

The health data 114 associated with the person may be analyzed at block 612, while an alert is generated at block 614. In some embodiments, the alert is generated based on a determination that the derivation has occurred. In some embodiment, the alert is generated based on when the activity pattern of the second time period from the activity pattern of the first time period exceeds the threshold and analysis of the health data 114. In some embodiments, the alert is transmitted, while in some embodiments the alert is stored.

Figure 7:
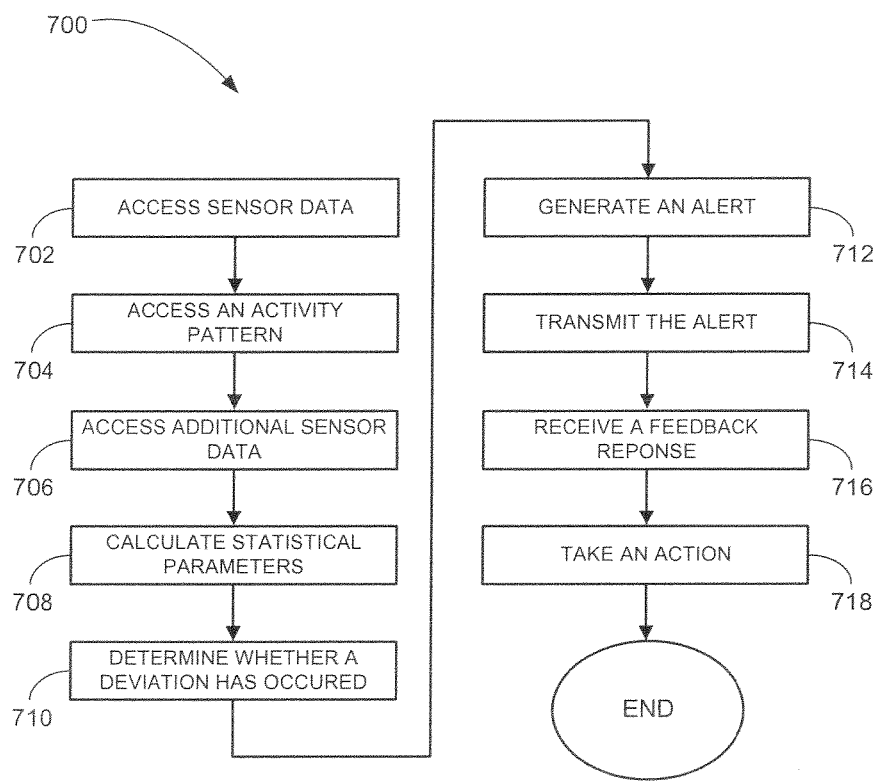

FIG. 7 illustrates a method 700 for sensor processing according to an example embodiment. The method 70 may be performed by the operator device 102 or the processor device 106 of the system 100 (see FIG. 1), or may be otherwise performed.

At block 702, the sensor data 112 is accessed from motion sensors and a bed sensor deployed in a living unit for a first time period.

An activity pattern for the first time period is identified at block 704 based on at least a portion of the sensor data 112 associated with the first time period. In some embodiments, the activity pattern represents a physical and cognitive health condition of a person residing in the living unit. In one embodiment, the activity pattern includes a single feature. In another embodiment, the activity pattern includes multiple features.

At block 706, additional sensor data 112 is accessed from the motion sensors and the bed sensor deployed in the living unit for a second time period. The second time period occurs after the first time period.

Statistical parameters of at least a portion of the sensor data 112 for the first time period are calculated at block 708.

A determination of whether a deviation of the activity pattern of the first time period has occurred for the second time period is performed at block 710. In some embodiments, the determination includes determining whether at least a portion of the additional sensor data 112 for the second time period is outside of a threshold. In general, the threshold is based on the statistical parameters.

An alert is generated at block 712 based on a determination that the derivation has occurred. In some embodiments, the alert is a hits-based alert. The activity pattern for the first time period may then be based on total number of sensor hits of a particular sensor 108 during a particular day of the first time period. In some embodiments, the alert is a time-based alert. The activity pattern for the first time period may then based on total time that a particular sensor 108 fired during a particular day of the first time period.

In some embodiments, the alert generated may be adapted or customized based on received feedback.

The alert including a link to a web interface may be transmitted at block 714. The web interface may include the sensor data 112 of the second time period in the context of the sensor data 112 of the first time period.

A feedback response may be received to the alert at block 716. The feedback response includes feedback regarding clinical relevance of the alert.

An action may be taken at block 718 based on receipt of the feedback response. In some embodiments, taking the action may include adjusting the threshold based on the receipt of the feedback response. In some embodiments, taking the action may include recording ignored indicia for the person based on the receipt of the feedback response. The ignored indicia may be associated with a feature of the alert.

Figure 8:
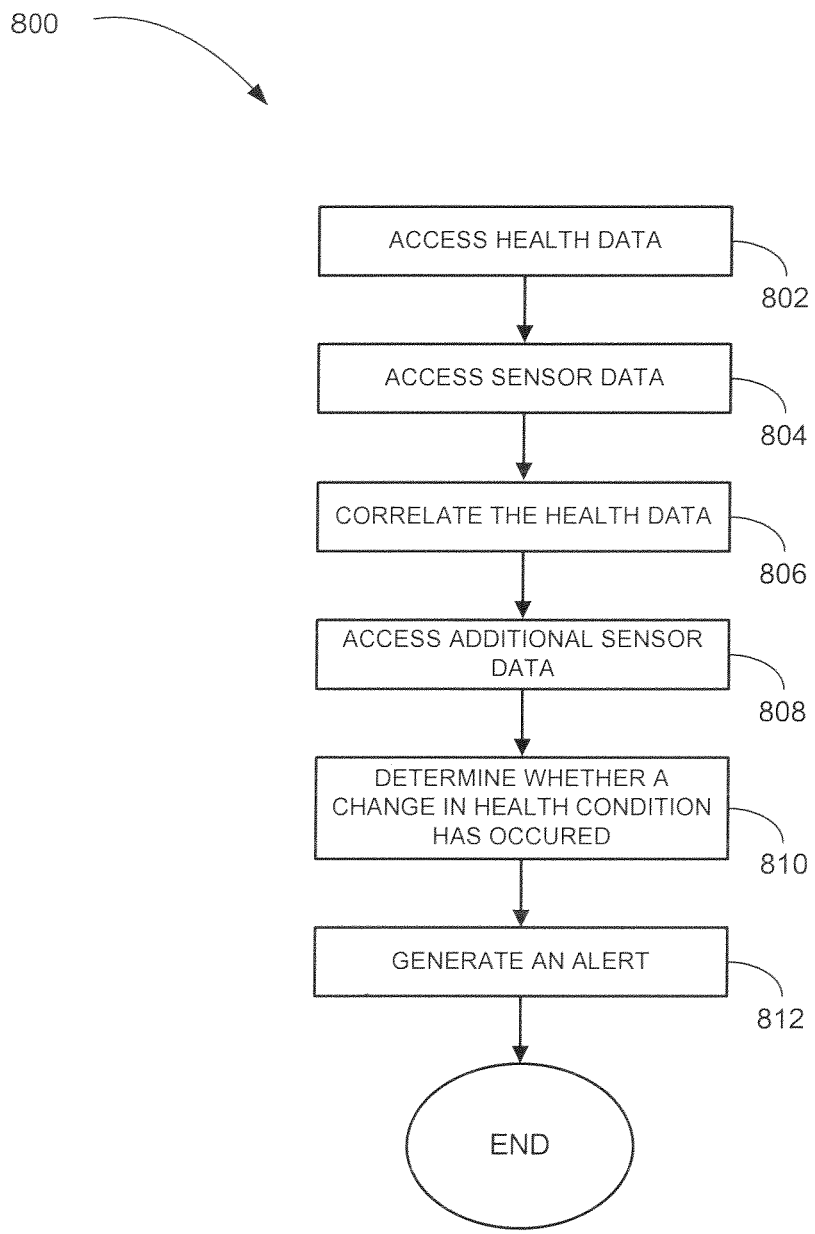

FIG. 8 illustrates a method 800 for sensor processing according to an example embodiment. The method 800 may be performed by the operator device 102 or the processor device 106 of the system 100 (see FIG. 1), or may be otherwise performed.

The health data 114 of a person for a first time period is accessed at block 802.

The sensor data 112 from motion sensors and a bed sensor deployed in a living unit for the first time period is accessed at block 804.

The health data is correlated to at least a portion of the sensor data 112 for the first time period at block 806.

Additional sensor data 112 is accessed at block 808 from the motion sensors and the bed sensor deployed in the living unit for a second time period. The second time period generally occurs after the first time period.

At block 810, a determination of whether a change in a health condition of the person has occurred is made based on the additional sensor data 112 and correlation of the health data 114 to at least the portion of the sensor data 112 for the first time period.

An alert may be generated at block 812 when a determination is made that the change in the health condition has occurred.

Figure 9:
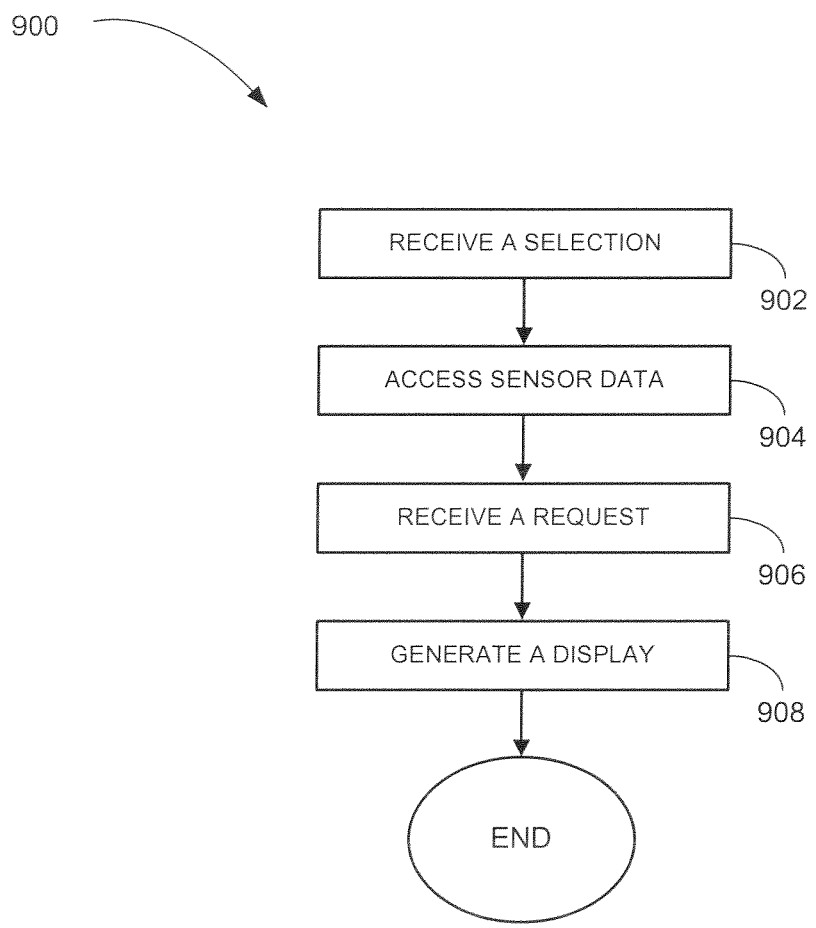
FIGS. 9 and 10 are block diagrams of flowcharts illustrating methods for display generation, according to example embodiments.

FIG. 9 illustrates a method 900 for display generation according to an example embodiment. The method 900 may be performed by the operator device 102 or the processor device 106 of the system 100 (see FIG. 1), or may be otherwise performed.

A selection of a person and/or a date range may be received at block 902.

The sensor data 112 is accessed from motion sensors and a bed sensor deployed in a living unit for a time period at block 904. In some embodiments, the access of the sensor data 112 from the motion sensors and the bed sensor for the time period is based on receipt of the selection.

A request may be received at block 906. In some embodiments, the request is a time interval modification request. In some embodiments, the request is a time increment modification request.

A display is generated at block 908 based on access of the sensor data 112 associated with the time period. In some embodiments, the sensor data 112 is grouped on the display based on multiple categories. For example, the categories may include motion, pulse, breathing, and restlessness.

In some embodiments, generation of the display is based on access of the sensor data 112 associated with the time period and receipt of the time interval modification request. In some embodiments, generation of the display is based on access of the sensor data 112 associated with the time period and receipt of the time increment modification request.

Figure 10:
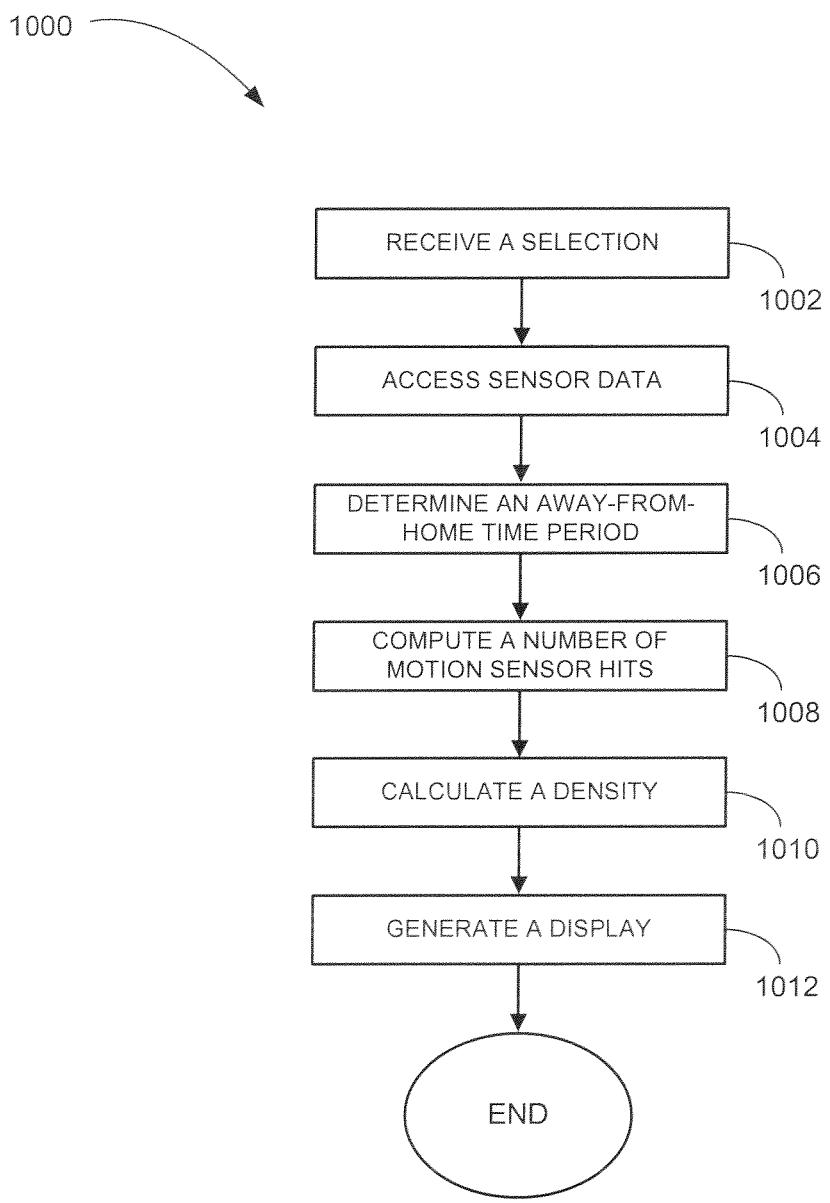

FIG. 10 illustrates a method 1000 for display generation according to an example embodiment. The method 1000 may be performed by the operator device 102 or the processor device 106 of the system 100 (see FIG. 1), or may be otherwise performed.

A selection of a person and/or a date range may be received at block 1002.

The sensor data 112 is accessed from motion sensors and a bed sensor deployed in a living unit for a time period at block 1004. In some embodiments, the access of the sensor data 112 from the motion sensors and the bed sensor for the time period is based on receipt of the selection.

A determination of an away-from-home time period for a person associated with the living unit during the time period is made at block 1006. In some embodiments, the determination of the away-from-home time period includes analyzing the sensor data 112 to determine whether a living unit departure sensor sequence and a living unit return sensor sequence has occurred and calculating a time difference between occurrence of the living unit departure sensor sequence and occurrence of the living unit return sensor sequence. The away-from home time period may then based on the time difference.

In one embodiment, analyzing the sensor data 112 includes applying fuzzy logic to at least a portion of the sensor data 112 to determine whether a living unit departure sensor sequence and a living unit return sensor sequence has occurred.

A number of motion sensor hits for multiple hours of the time period may be computed at block 1008. A single motion sensor hit is associated with a single motion sensor of the plurality of motion sensors.

A density for the hours may be calculated at block 1010. The density for an hour may be based on the number of motion sensor hits during the hour and the determination of the away-from-home time period.

A display is generated at block 1012 based on access of the sensor data 112 associated with the time period and a determination of the away-from-home time period. In some embodiments, generation of the display is based on calculation of the density.

In some embodiments, generation of the display includes selecting a color mappings and generating the display based on selection of the color mappings. In general, a color mapping has a color based on the density and is associated with a position based on an hour of a day.

Figure 11:
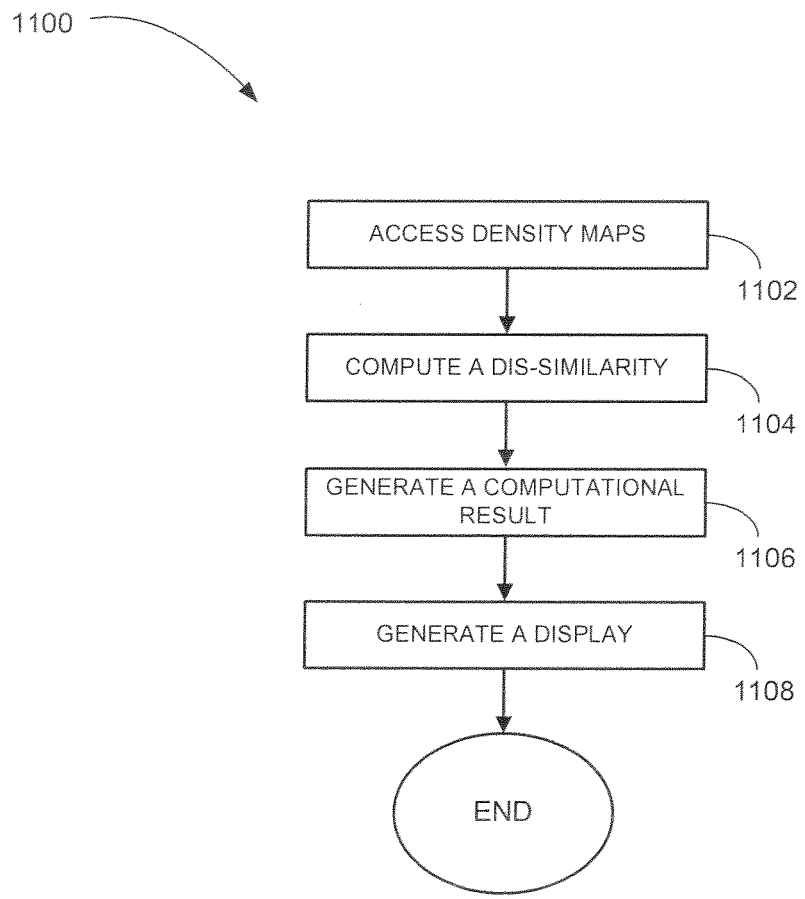
FIG. 11 is a block diagram of a flowchart illustrating a method for determining dis-similarity of density maps, according to an example embodiment.

FIG. 11 illustrates a method 1100 for determining dissimilarity of density maps according to an example embodiment. The method 1100 may be performed by the operator device 102 or the processor device 106 of the system 100 (see FIG. 1), or may be otherwise performed.

A dis-similarity measure based on texture features may be used for comparing density maps and automatically determining changes in activity patterns. The dis-similarity between two density maps may be computed to aid caregivers in evaluating changes of residents. The texture features may be used evaluate the dis-similarity of density maps by capturing spatial, frequency, and perceptual properties such as periodicity, coarseness, and complexity. Texture features may be extracted using the co-occurrence distribution (e.g., the gray-level co-occurrence statistical method using the density values directly).

In some embodiments, the density maps need not have the color mapping to determine the dis-similarity.

A first density map and a second density map are accessed at block 1102. The first density map has first color mappings. The second density map has second color mappings. In general, a color mapping has a color based on density and is associated with a position based on an hour of a day. In some embodiments, the density is based on a number of motion sensor hits during the hour and a determination of the away-from-home time period.

A dis-similarity between the first density map and the second density map is computed at block 1104 based on a textual feature of the first density map and the second density map. Examples of textual features include spatial, frequency, and perceptual properties. The computation may be performed based on a single textual feature or multiple textual features.

An angular second moment feature (ASM) may measure homogeneity of the image. The contrast feature may measure the amount of local variations in an image. The inverse difference moment may also measure image homogeneity. Entropy may measure the disorder. Other non-textual features may also be used to discriminate the dis-similarity of density maps. For example, average motion density per hour and average time away from the living unit per day may be used during the computation performed at block 1104.

The dis-similarity of two different density maps, in some embodiments, is represented by a number that is computed in feature space as the distance from one map to another.

A computational result is generated at block 1106 based on computing the dis-similarity.

A display may be generated at block 1108 based on computation of the dis-similarity. In some embodiments, a notification based on computation of the dis-similarity may be transmitted. In some embodiments, the computational result may be stored.

Figure 12:
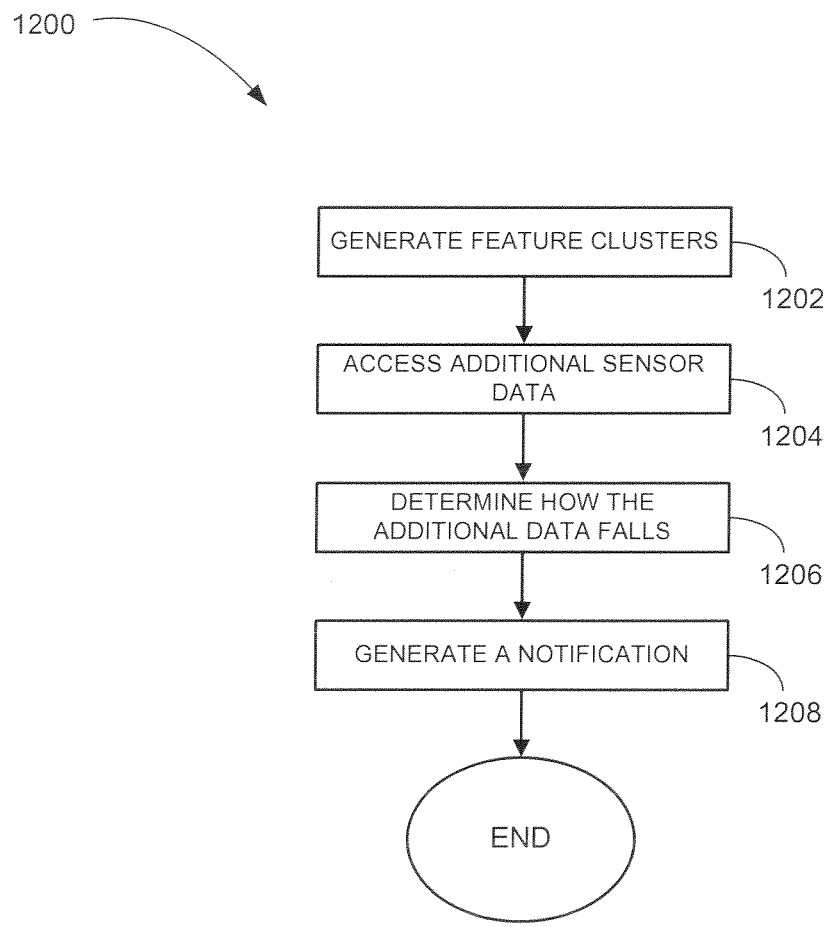
FIG. 12 is a block diagram of a flowchart illustrating a method for performing cluster analysis, according to an example embodiment.

FIG. 12 illustrates a method 1200 for performing cluster analysis according to an example embodiment. The method 1200 may be performed by the operator device 102 or the processor device 106 of the system 100 (see FIG. 1), or may be otherwise performed.

Feature clusters are generated for a time period at block 1202. The time period includes multiple days. A feature cluster is associated with a multiple feature vectors. A feature vector is associated with the sensor data 112 from at least some of the motion sensors and/or a bed sensor deployed in a living unit.

Additional sensor data 112 associated with a particular feature for a different time period is accessed at block 1204.

A determination of whether the additional sensor data 112 falls within the feature clusters or belongs in a new cluster is made at block 1206.

A notification is generated at block 1208 based on a result of a determination.

In some embodiments, a cluster addition notification is generated based on a determination that the additional sensor data 112 falls within the feature clusters. In some embodiments, a new cluster notification is generated based on a determination that the additional sensor data 112 belongs in the new cluster.

Figure 13:
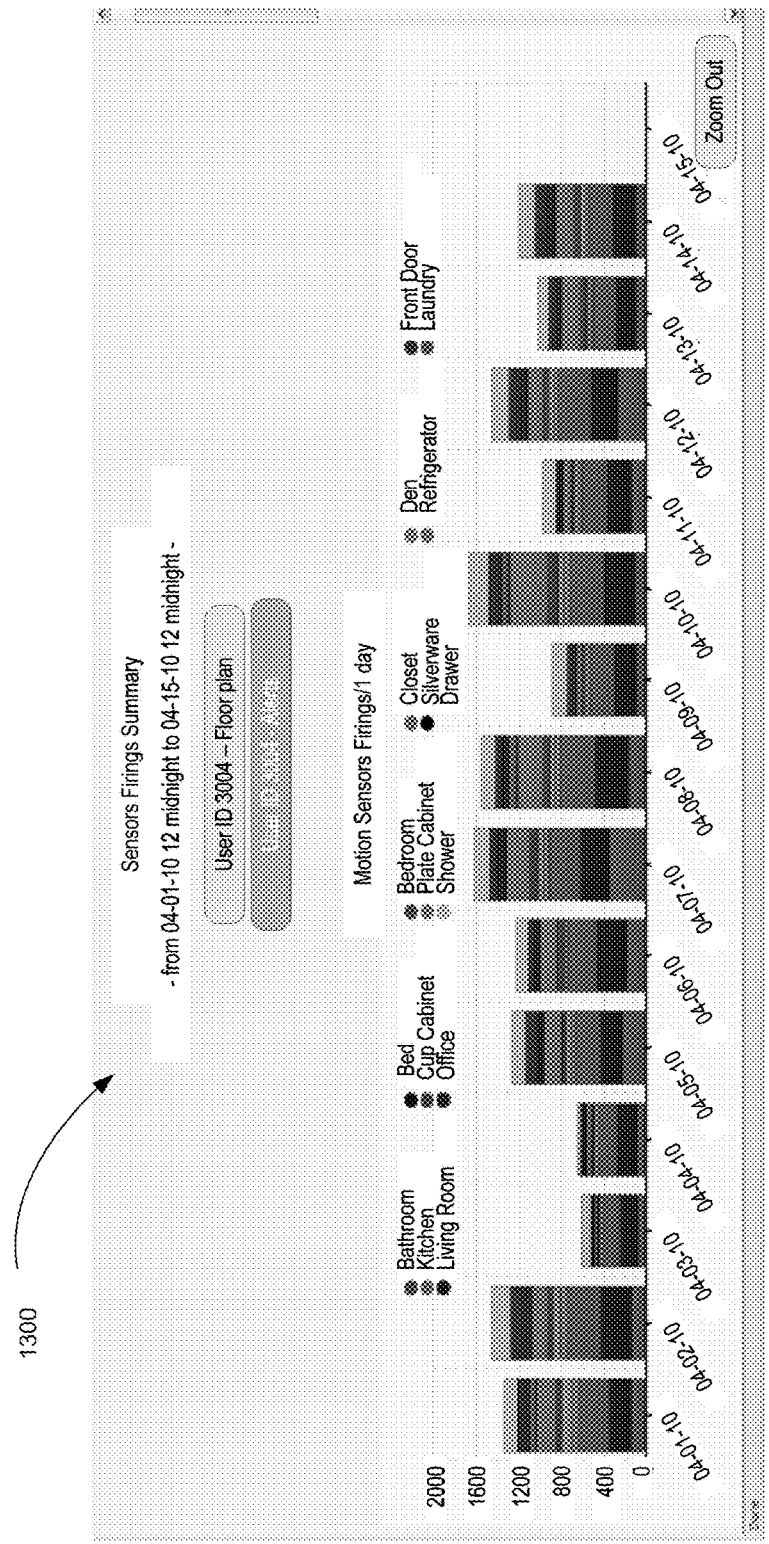
FIGS. 13-27 are diagrams, according to example embodiments.

FIG. 13 is a diagram 1300 of a user interface, according to an example embodiment. The user interface shows motion sensor data for multiple sensors over a period of fourteen days.

Figure 14:
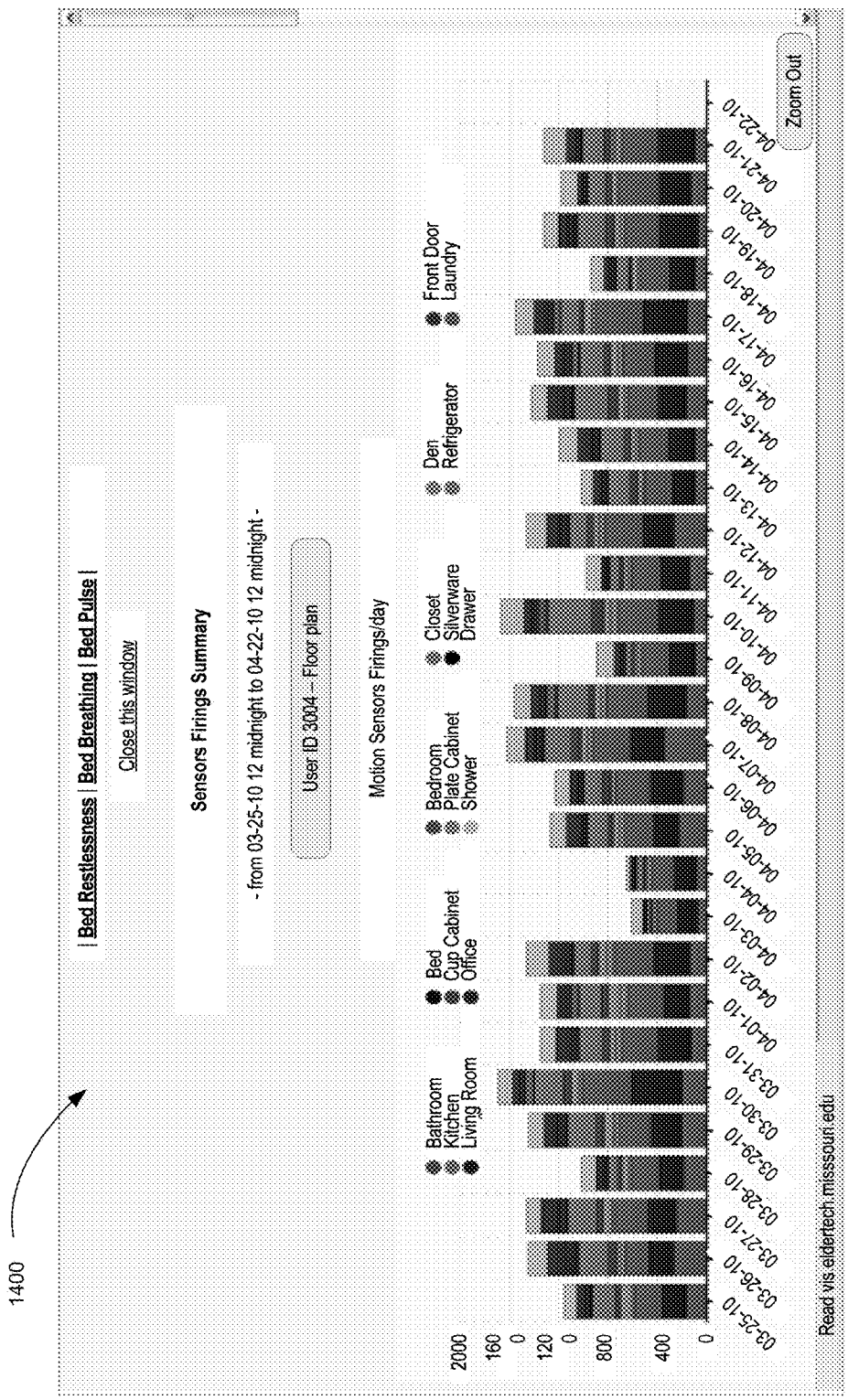

FIG. 14 is a diagram 1400 of a user interface, according to an example embodiment. The user interface shows motion sensor data over a period of twenty eight days. The diagram 1400 is a "zoomed out" version of the diagram 1300 (see FIG. 13).

Figure 15:
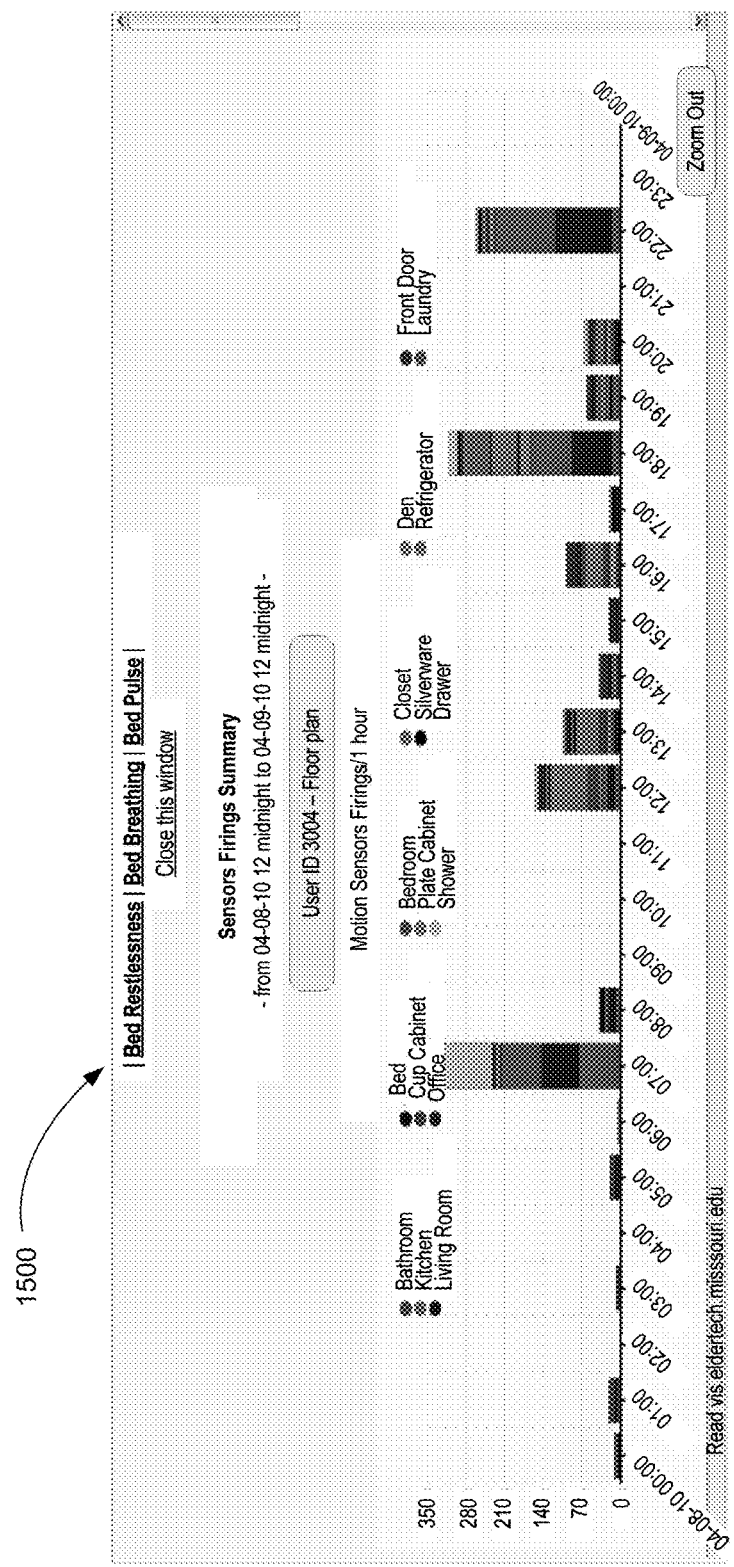

FIG. 15 is a diagram 1500 of a user interface, according to an example embodiment. The user interface shows motion sensor data over a period of a day. The diagram 1500 is a "zoomed in" version of the diagram 1300 (see FIG. 13).

Figure 16:
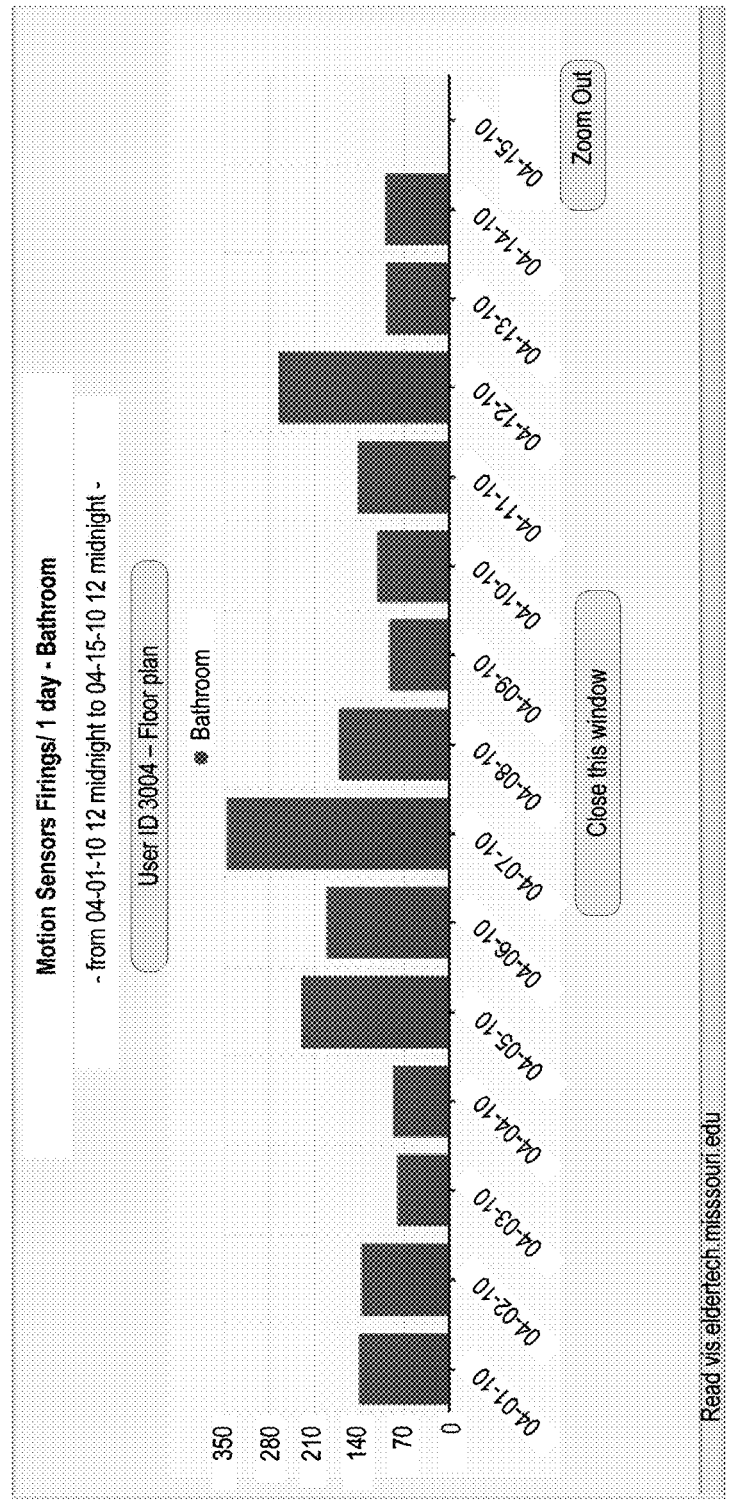

FIG. 16 is a diagram 1600 of a user interface, according to an example embodiment. The user interface shows motion sensor data for a single sensor over a period of fourteen days.

Figure 17:
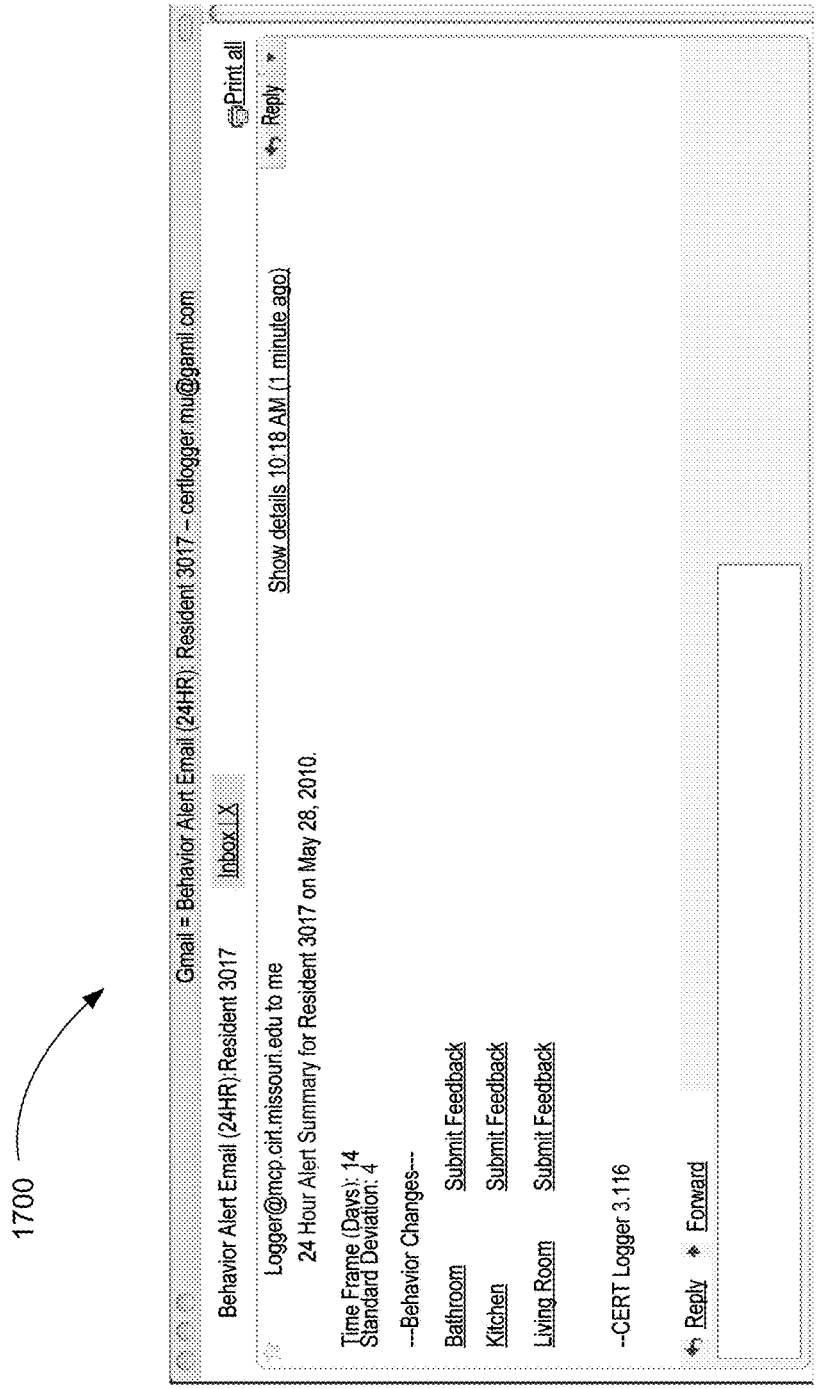

FIG. 17 is a diagram 1700 of an example alert, according to an example embodiment. The alert shown the diagram 1700 may be transmitted as an e-mail or otherwise transmitted. The alert is shown to include links to a user interface associated with sensors. The links included in the diagram are a link to a bathroom sensor, a kitchen sensor, and a living room sensor. In the example alert shown in the diagram 1700, links are also included to feedback web pages to capture a user's rating of the significance of the alert.

Figure 18:
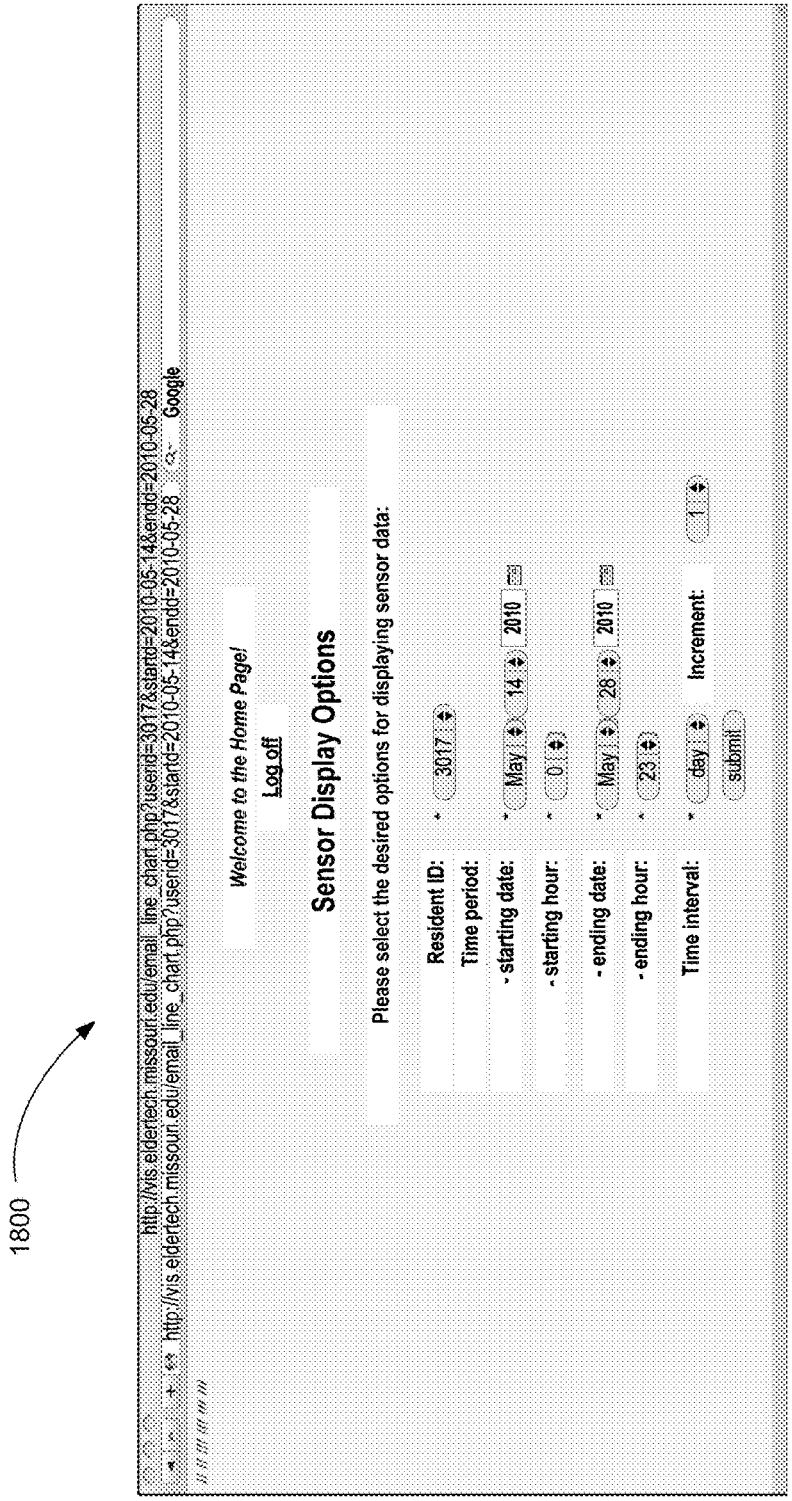

FIG. 18 is a diagram 1800 of a user interface, according to an example embodiment. The diagram 1800 shows a user interface that may be presented based on selection of a link included in an alert of the diagram 1700.

As shown in the diagram 1800, a resident ID, a time period including starting date, starting hour, ending date, and ending hour, a time interval, and an increment selections may be available for customization. The operator may modify default selections and then press a submit button.

Figure 19:
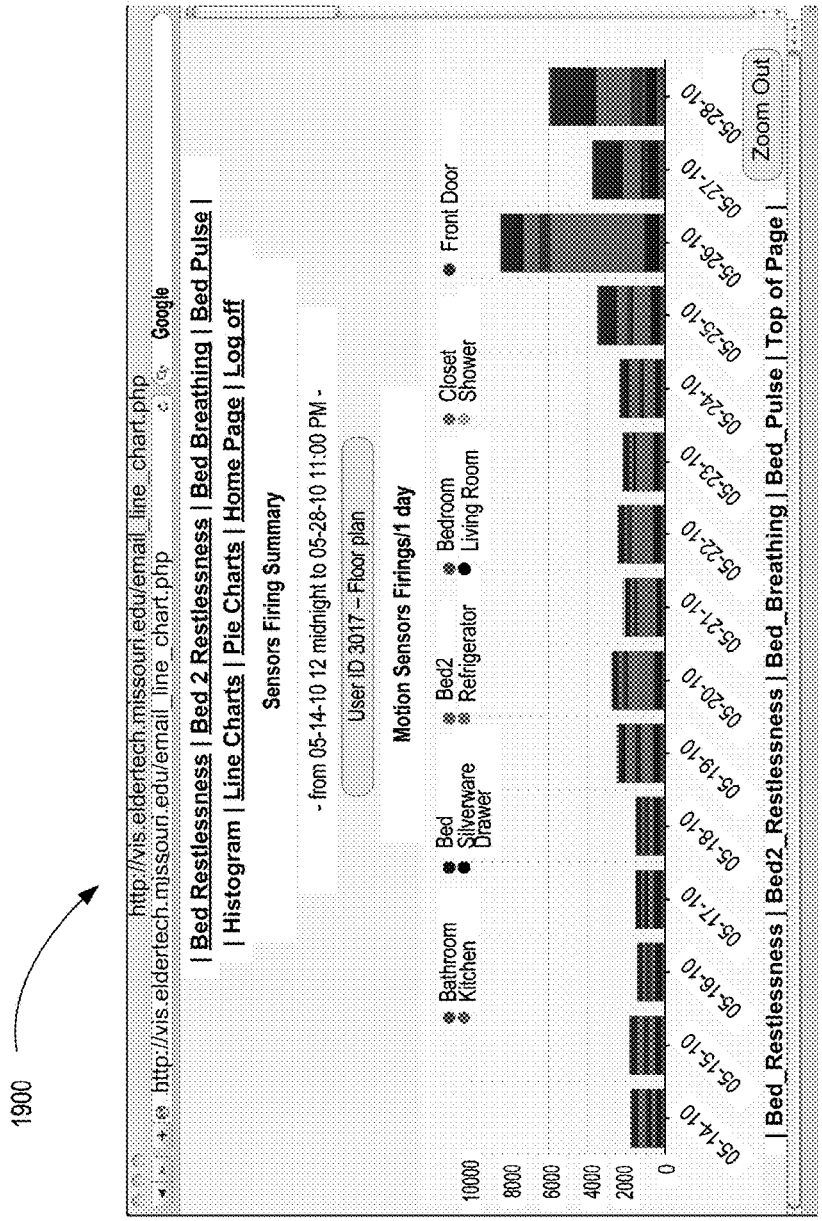

FIG. 19 is a diagram 1900 of a user interface, according to an example embodiment. The diagram 1900 shows sensor firing data for a fourteen day period. The diagram 1900 may be presented based on selection of a submit button from the diagram 1800.

Figure 20:
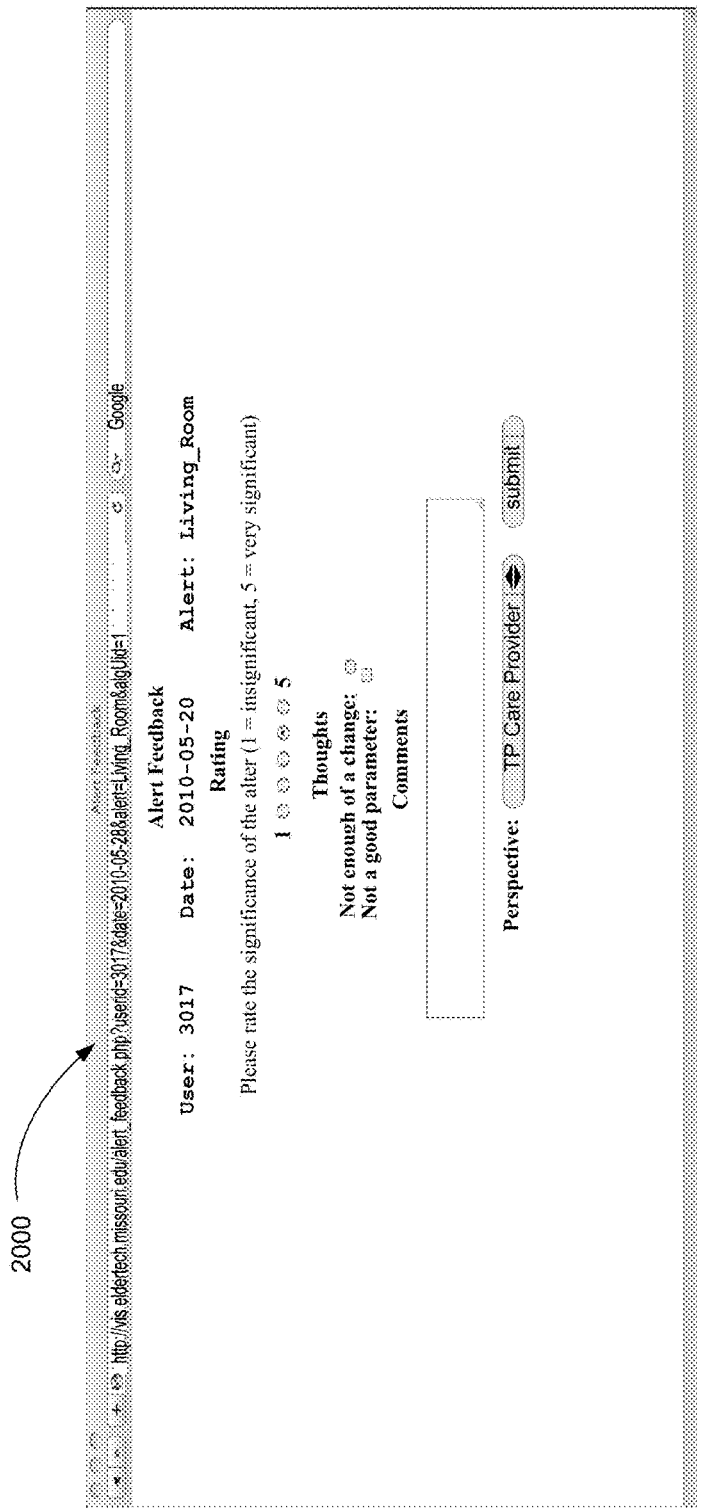

FIG. 20 is a diagram 2000 of a user interface, according to an example embodiment. The diagram enables an operator to provide alert feedback. The operator may include a rating of the significance of the alert, thoughts about the alert (e.g., not enough of a change and not a good parameter), and comments through the user interface. Other or different feedback may be collected. The operator may also designate the perspective (e.g., classification) of the operator submitting the feedback.

In some embodiments, the user interface shown in the diagram 2000 may be used to provide adaptive, customizable alerts by adjusting the sensor parameters and thresholds, based on the alert feedback ratings.

Figure 21:
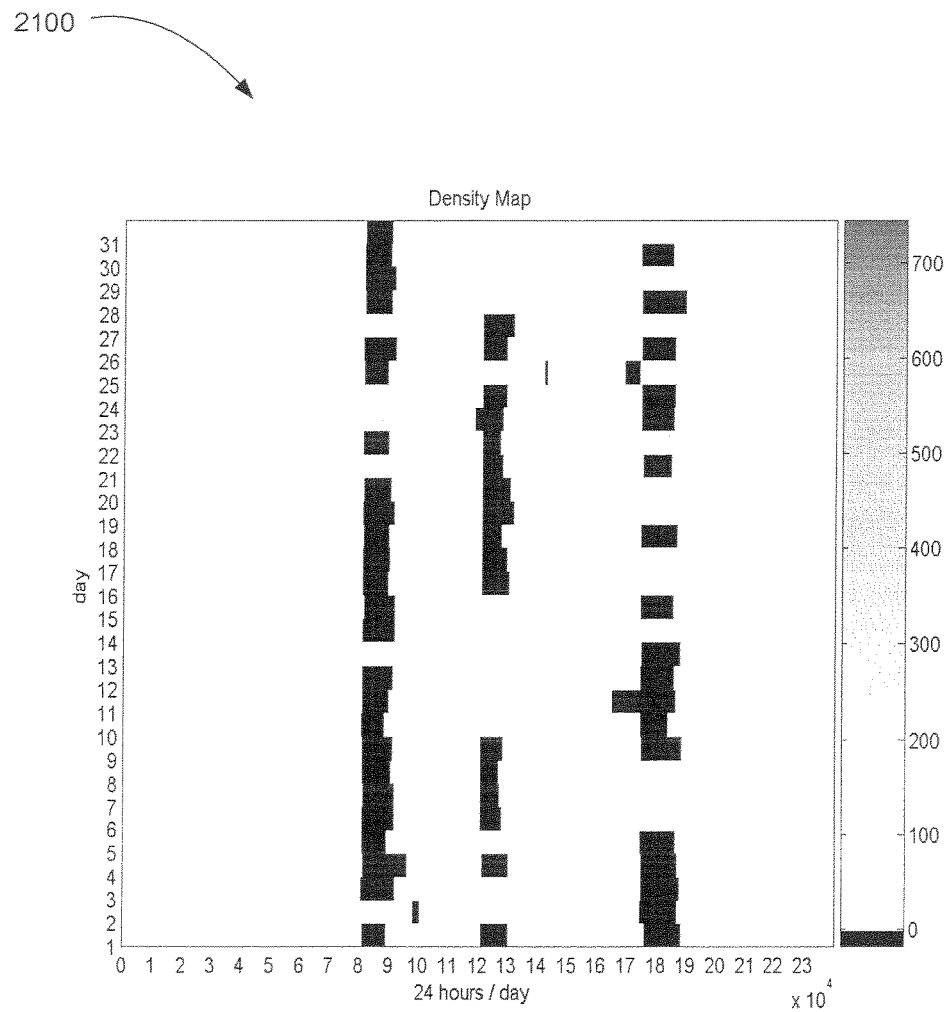
Figure 22:
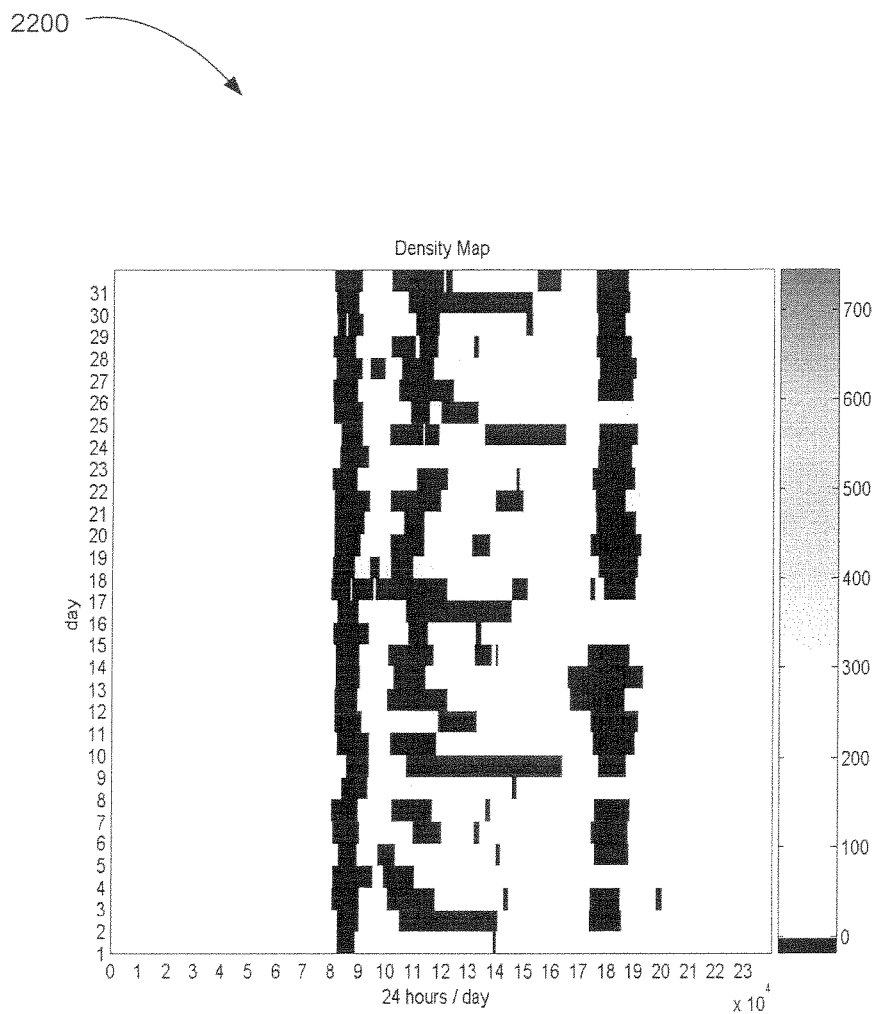
Figure 23:
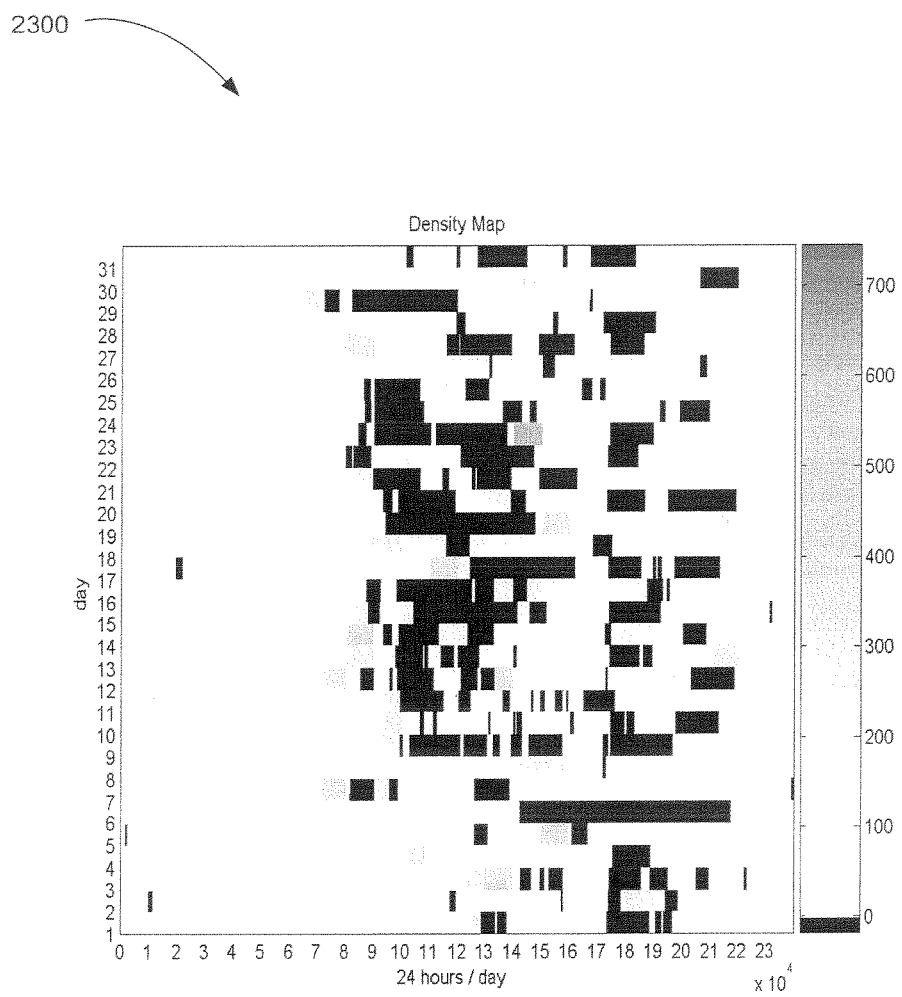

FIGS. 21-23 are diagrams 2100-2300 of density maps, according to an example embodiment. While the diagrams 2100-2300 are shown in this document in black and white, the displays associated with the diagrams 2100-2300 are typically generated in color based on color mappings.

The diagram 2100 is a density map of a person with a sedentary lifestyle pattern for one month. The diagram 2200 is a density map of a person with an active lifestyle pattern for one month. The diagram 2300 is a density map of a person with an irregular lifestyle pattern showing a cognitive problem for one month.

Figure 24:
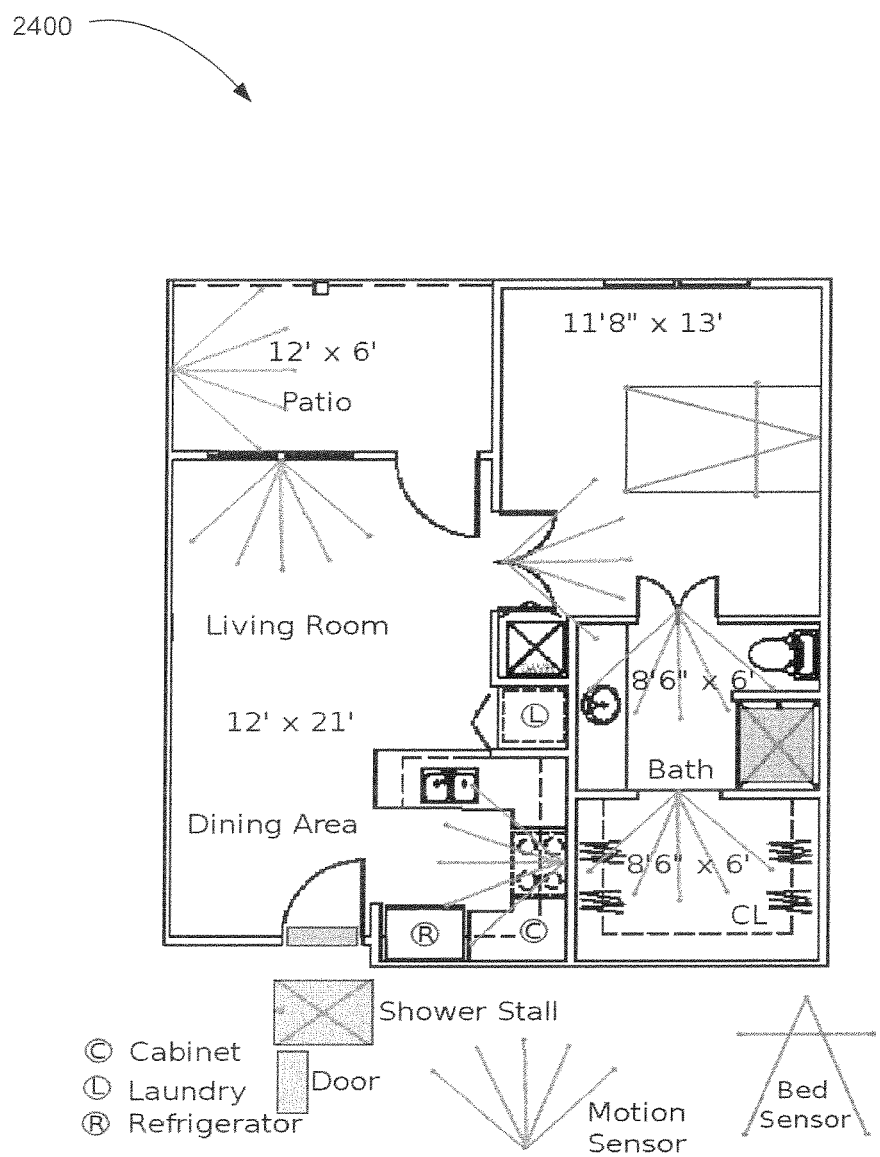

By monitoring the motion density maps over time, health care providers in some embodiments may identify a typical pattern of activity for an individual and watch for changes in the pattern FIG. 24 is a diagram 2400 of a floor plan of living unit, according to an example embodiment. The diagram 2400 shows example locations of motion sensors, a bed sensor, and a stove sensor in the living unit.

The motion sensors may detect presence in a particular room as well as specific activities. For example, a motion sensor installed on the ceiling above the shower detects showering activity; motion sensors installed discretely in cabinets and the refrigerator detect kitchen activity. For convenience, a motion sensor may also installed on the ceiling above the door of the living unit, to detect movement in and out of the doorway (e.g., for living unit exits). The motion sensors, in some embodiments, are commercially available passive infrared (PIR) sensors which transmit using the wireless X10 protocol. Other types of sensors may be used.

In some embodiments, the sensors detect movement of warm bodies and transmit an event about every 7 seconds when movement is still detected. This artifact is useful for capturing a general lifestyle pattern; for example, a sedentary pattern will result in a smaller number of sensor events over time compared to a more active "puttering" pattern.

The bed sensor may be a transducer which detects presence in the bed, pulse and respiration rates, and bed restlessness. Pulse and respiration rates may be reported as low, normal, and high, based on thresholds, or pulse and respiration rates may be reported as numerical rates. In some embodiments, bed restlessness is reported based on the persistence of movement in the bed. All of the output of the bed sensor may contribute to the general pattern of the resident.

The stove sensor may detect motion in the kitchen as well as the temperature of the stove/oven unit. This may be performed through a modified X10 PIR motion sensor. When a high temperature is detected, a "stove on" event may be generated. When the temperature drops below a threshold again, a "stove off" event may be generated. This sensor is included so that an alert could be generated if the stove is left on and there is no indication of someone in the kitchen for a specified period of time.

In some embodiments, all of the sensor data 112 for the person is transmitted wirelessly via the X10 protocol to a data monitor PC which is located in the living unit of the person. The data monitor may add a date-time stamp for each sensor event and may log it as the sensor data into a file that is periodically sent to a dedicated central server which stores the data in a relational database. The data monitors may be connected to the central server through a dedicated local network, for security purposes. In addition, as a precaution, identifiers may be stripped from the data before transmission.

Figure 25:
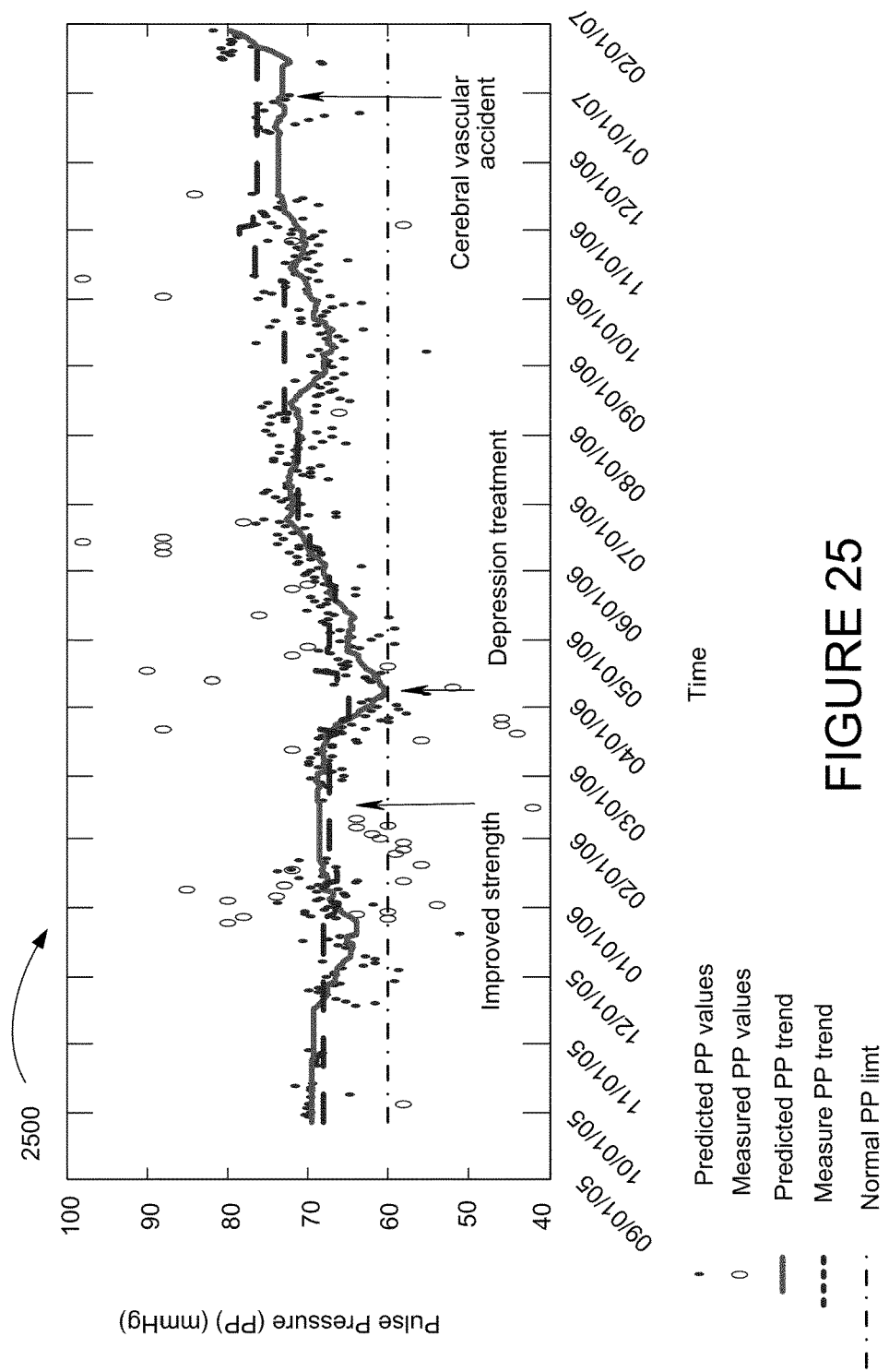
Figure 26:
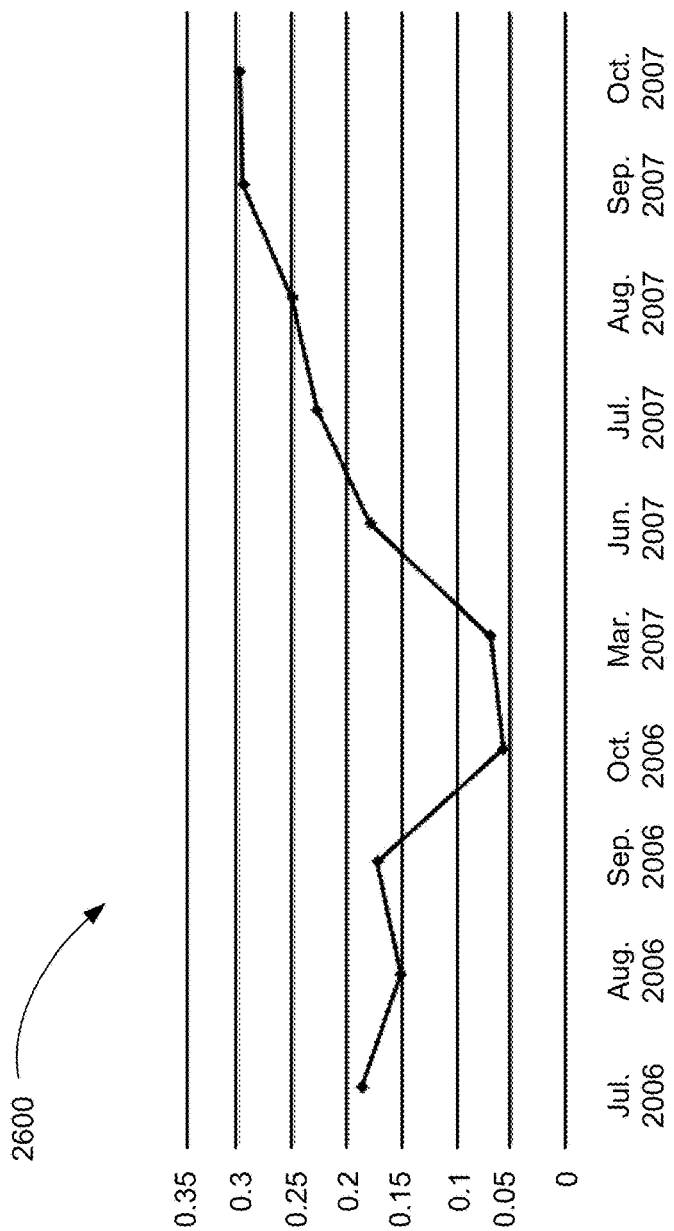

FIG. 25 is a diagram 2500 of predicted pulse pressure from the sensor data 112 and measured pulse pressure, according to an example embodiment FIG. 26 is a diagram 2600 of a comparison of Euclidean distance for a person, according to an example embodiment. The diagram 2600 may be generated as a result of the operations performed at block 1108 (see FIG. 11).

Figure 27:
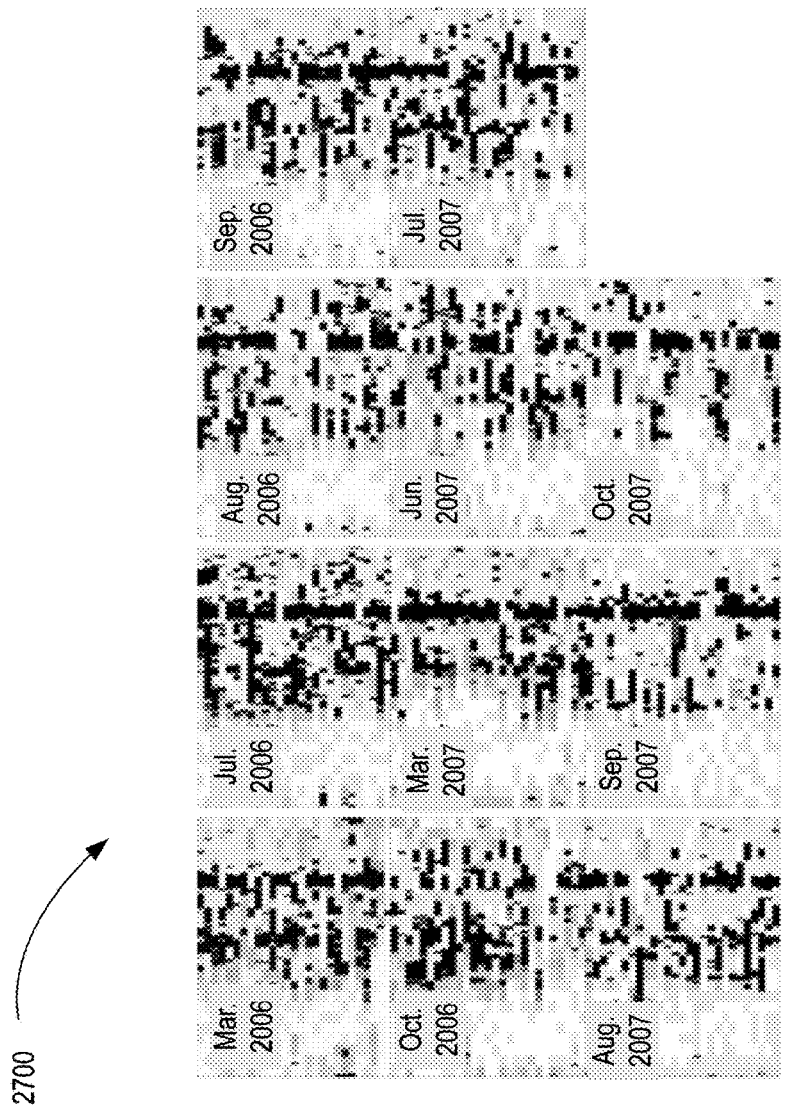

FIG. 27 is a diagram 2700 of multiple density maps associated with for the diagram 2600.

Figure 28:
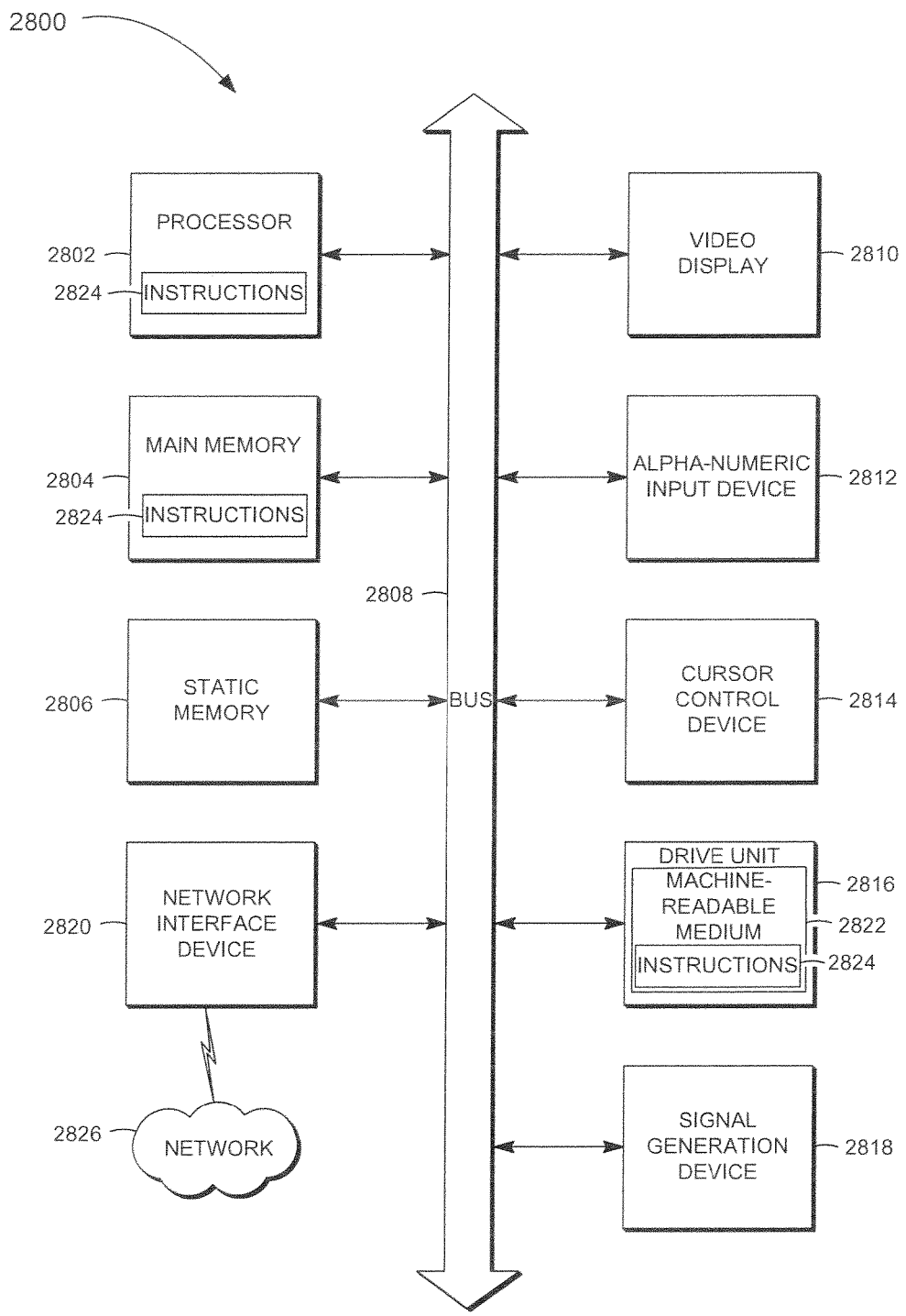
FIG. 28 is a block diagram of a machine in the example form of a computer system within which a set of instructions for causing the machine to perform any one or more of the methodologies discussed herein may be executed.

FIG. 28 shows a block diagram of a machine in the example form of a computer system 2800 within which a set of instructions may be executed causing the machine to perform any one or more of the methods, processes, operations, or methodologies discussed herein. The operator device 102, the provider device 106, or both may include the functionality of the one or more computer systems 2800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, a kiosk, a point of sale (POS) device, a cash register, an Automated Teller Machine (ATM), or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2800 includes a processor 2812 (e.g., a central processing unit (CPU) a graphics processing unit (GPU) or both), a main memory 2804 and a static memory 2806, which communicate with each other via a bus 2808. The computer system 2800 may further include a video display unit 2810 (e.g., a liquid crystal display (LCD) or a cathode ray tube (CRT)). The computer system 2800 also includes an alphanumeric input device 2812 (e.g., a keyboard), a cursor control device 2814 (e.g., a mouse), a drive unit 2816, a signal generation device 2818 (e.g., a speaker) and a network interface device 2820.

The drive unit 2816 includes a machine-readable medium 2822 on which is stored one or more sets of instructions (e.g., software 2824) embodying any one or more of the methodologies or functions described herein. The software 2824 may also reside, completely or at least partially, within the main memory 2804 and/or within the processor 2812 during execution thereof by the computer system 2800, the main memory 2804 and the processor 2812 also constituting machine-readable media.

The software 2824 may further be transmitted or received over a network 2826 via the network interface device 2820.

While the machine-readable medium 2822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing or encoding a set of instructions for execution by the machine and that cause the machine to perform any one or more of the methodologies of the present invention. The term "machine-readable medium" shall accordingly be taken to include, but not be limited to, solid-state memories, and optical media, and magnetic media. In some embodiments, the machine-readable medium is a non-transitory machine readable medium.

Certain systems, apparatus, applications or processes are described herein as including a number of modules. A module may be a unit of distinct functionality that may be presented in software, hardware, or combinations thereof. When the functionality of a module is performed in any part through software, the module includes a machine-readable medium. The modules may be regarded as being communicatively coupled.

In an example embodiment, sensor data may be accessed from a plurality of motion sensors and a bed sensor deployed in a living unit for a first time period. An activity pattern for the first time period may be identified based on at least a portion of sensor data associated with the first time period. The activity pattern may represent a physical and cognitive health condition of a person residing in the living unit.

Additional sensor data may be accessed from the plurality of motion sensors and the bed sensor deployed in the living unit for a second time period. The second time period may occur after the first time period. A determination of whether a deviation of the activity pattern of the first time period has occurred for the second time period may be performed. An alert may be generated based on a determination that the derivation has occurred.

In an example embodiment, health data of a person may be accessed for a first time period. Sensor data from a plurality of motion sensors and a bed sensor deployed in a living unit may be accessed for the first time period. The person may live in the living unit. Health data may be correlated to at least a portion of the sensor data for the first time period. Additional sensor data may be accessed from the plurality of motion sensors and the bed sensor deployed in the living unit for a second time period. The second time period may occurring after the first time period. A determination of whether a change in a health condition of the person has occurred may be made based on the additional sensor data and correlation of the health data to at least the portion of the sensor data for the first time period.

In an example embodiment, sensor data may be accessed from a plurality of motion sensors and a bed sensor deployed in a living unit for a time period. A display may be generated based on access of the sensor data associated with the time period.

In an example embodiment, a first density map and a second density map may be accessed. The first density map may have a plurality of first color mappings. The second density map may have a plurality of second color mappings. A particular first color mapping may have a color based on density and being associated with a position based on a particular hour and a particular day. Density may be based on a number of motion sensor hits during the particular hour and a determination of the away-from-home time period. A dis-similarity between the first density map and the second density map may be computed based on a textual feature of the first density map and the second density map. A computational result may be generated based on computing the dis-similarity.

In an example embodiment, a plurality of feature clusters may be generated for a time period. The time period may include a plurality of days. A particular feature cluster may be associated with a plurality of feature vectors. A particular feature vector may be associated with sensor data from at least some of a plurality of motion sensors and a bed sensor deployed in a living unit. Additional sensor data associated a particular feature for a different time period may be accessed. A determination of whether the additional sensor data falls within the plurality of feature clusters or belongs in a new cluster may be made. A notification may be generated based on a result of a determination.

Thus, methods and systems for an integrated network have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

Various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
    processing sensor data from a plurality of motion sensors and a bed sensor deployed in a living unit for a first time period to establish a frame of reference for an activity pattern by a person residing in the living unit, wherein the activity pattern frame of reference represents a health condition of a person residing in the living unit, wherein the processed sensor data for the first time period comprises a plurality of data values corresponding to a plurality of subintervals within the first time period, wherein each subinterval data value represents (1) a total number of sensor hits during that subinterval of the first time period or (2) a total time for sensor firings during that subinterval of the first time period, and wherein the activity pattern frame of reference comprises a statistical value about the subinterval data values over the first time period;
    computing a standard deviation for the processed sensor data over the first time period based on the subinterval data values;
    defining a statistical parameter threshold, wherein the statistical parameter threshold comprises a defined number of the standard deviations;
    processing additional sensor data from the plurality of motion sensors and the bed sensor deployed in the living unit for a second time period, the second time period occurring after the first time period;
    computing a value for the activity pattern for the second time period based on the processed additional sensor data, the computed activity pattern value of the second time period also representing a health condition of the person, wherein the computed activity pattern value comprises (1) data about a total number of sensor hits during the second time period if the activity pattern frame of reference is based on the total number of sensor hits during the first time period or (2) data about a total time for sensor firings during the second time period if the activity pattern frame of reference is based on the total time for sensor firings during the first time period;
    comparing the computed activity pattern value with the activity pattern frame of reference and the defined statistical parameter threshold to determine whether the computed activity pattern value deviates from the activity pattern frame of reference by more than the defined number of the standard deviations;
    generating an alert based on a determination that the computed activity pattern value deviates from the activity pattern frame of reference by more than the defined number of standard deviations;

receiving a feedback response to the alert, the feedback response including feedback regarding clinical relevance of the alert; and adjusting the defined number of the standard deviations for the statistical parameter threshold to a different defined number of the standard deviations based on the feedback response to the alert.

2. A method of comprising:

accessing sensor data from a plurality of motion sensors and a bed sensor deployed in a living unit for a first time period, wherein the accessed sensor data comprises a total number of sensor hits during the first time period;

identifying an activity pattern for the first time period based on the total number of sensor hits during the first time period, the activity pattern of the first time period representing a health condition of a person residing in the living unit, and wherein the activity pattern for the first time period comprises a plurality of first time period data values, wherein each first time period data value corresponds to a subinterval of the first time period and is indicative of a total number of sensor hits for its corresponding subinterval of the first time period;

accessing additional sensor data from the plurality of motion sensors and the bed sensor deployed in the living unit for a second time period, the second time period occurring after the first time period, wherein the first time period is longer than the second time period, and wherein the accessed additional sensor data comprises a total number of sensor hits during the second time period;

identifying an activity pattern for the second time period based on the total number of sensor hits during the second time period, the activity pattern of the second time period also representing a health condition of the person;

calculating statistics about the first time period data values, the calculated statistics including a standard deviation for the first time period data values;

defining a statistical parameter threshold, wherein the statistical parameter threshold comprises a defined number of the standard deviations;

analyzing the activity pattern of the second time period with respect to the statistical parameter threshold, wherein the analyzing step comprises comparing a data value indicative of a total number of sensor hits for the second time period with the calculated statistics to determine whether the second time period data value exceeds a calculated statistic about the first time period data values by more than the threshold number of the standard deviations;

generating an alert in response to the second time period data value exceeding the calculated statistic about the first time period data values by more than the threshold number of the standard deviations;

receiving a feedback response to the alert, the feedback response including feedback regarding clinical relevance of the alert; and adjusting the defined number of the standard deviations for the statistical parameter threshold to a different defined number of the standard deviations based on the feedback response to the alert.

3. The method of claim 2, wherein the activity pattern includes a plurality of features and the deviation is associated with a particular feature of the plurality of features.

4. The method of claim 2, further comprising:

recording ignored indicia for the person based on the receipt of the feedback response; and determining whether the deviation has occurred based in part on the recorded ignored indicia.

5. The method of claim 2, further comprising:

analyzing health data associated with the person;

wherein generation of the alert is based on (1) when the deviation exceeds the statistical parameter threshold and (2) an analysis of the health data.

6. The method of claim 2, further comprising:

accessing the sensor data from a stove sensor deployed in the living unit; and accessing the additional sensor data from the stove sensor deployed in the living unit.

7. The method of claim 2, wherein the plurality of motion sensors and the bed sensor are passive, non-wearable sensors.

8. The method of claim 2, further comprising:

identifying at least a portion of the sensor data associated with the first time period as being associated with the person;

wherein identification of the activity pattern for the first time period is based on at least the portion of sensor data associated with the first time period associated with the person.

9. The method of claim 1, wherein the first time period has a same time duration as the second time period.

10. The method of claim 2, wherein the calculating step comprises calculating the statistical parameters of at least a portion of the sensor data for the first time period; and wherein the statistical parameter threshold is an individualized statistical parameter threshold.

11. The method of claim 2, further comprising:

transmitting the alert including a link to a web interface, the web interface including the sensor data of the second time period in the context of the sensor data of the first time period.

12. The method of claim 2, further comprising:

adjusting a sensor parameter used for the alert based on the receipt of the feedback response.

13. The method of claim 2, wherein the activity pattern includes a plurality of features.

14. The method of claim 1, wherein the activity patterns of the first and second time periods are based on the total number of sensor hits during the first and second time periods.

15. The method of claim 1, wherein the activity patterns of the first and second time periods are based on the total time for sensor firings during the first and second time periods.

16. The method of claim 2, wherein the activity patterns of the first and second time periods are based on a density of sensor hits during the first and second time periods.

17. The method of claim 16, wherein the calculating step includes calculating a dis-similarity between the activity pattern densities as between the first and second time periods.

18. The method of claim 17, wherein the dis-similarity calculating comprises calculating the dis-similarity based on at least one member of the group consisting of a spatial frequency and perceptual property of the activity pattern densities.

19. The method of claim 2 wherein the subinterval corresponds to a daily subinterval within the first time period.

20. The method of claim 2 wherein the second time period is the same as the subinterval.

21. The method of claim 2 further comprising:
providing a user interface through which a user can adjustably define a plurality of parameters for the sensor data;
defining the first time period and the subinterval in response to user input through the provided user interface.

22. The method of claim 21 wherein the providing step comprises providing the user interface in response to user input with respect to the alert.

23. A method of comprising:
accessing sensor data from a plurality of motion sensors and a bed sensor deployed in a living unit for a first time period, wherein the accessed sensor data comprises a total time for sensor firings during the first time period;
identifying an activity pattern for the first time period based on the total time for sensor firings during the first time period, the activity pattern of the first time period representing a health condition of a person residing in the living unit, and wherein the activity pattern for the first time period comprises a plurality of first time period data values, wherein each first time period data value corresponds to a subinterval of the first time period and is indicative of a total time for sensor firings for its corresponding subinterval of the first time period;
accessing additional sensor data from the plurality of motion sensors and the bed sensor deployed in the living unit for a second time period, the second time period occurring after the first time period, wherein the first time period is longer than the second time period, and wherein the accessed additional sensor data comprises a total time for sensor firings during the second time period;
identifying an activity pattern for the second time period based on the total time for sensor firings during the second time period, the activity pattern of the second time period also representing a health condition of the person;
calculating statistics about the first time period data values, the calculated statistics including a standard deviation for the first time period data values;
defining a statistical parameter threshold, wherein the statistical parameter threshold comprises a defined number of the standard deviations;
analyzing the activity pattern of the second time period with respect to the statistical parameter threshold, wherein the analyzing step comprises comparing a data value indicative of a total time for sensor firings for the second time period with the calculated statistics to determine whether the second time period data value exceeds a calculated statistic about the first time period data values by more than the threshold number of the standard deviations;
generating an alert in response to the second time period data value exceeding the calculated statistic about the first time period data values by more than the threshold number of the standard deviations;
receiving a feedback response to the alert, the feedback response including feedback regarding clinical relevance of the alert; and
adjusting the defined number of the standard deviations for the statistical parameter threshold to a different defined number of the standard deviations based on the feedback response to the alert.

24. The method of claim 23 wherein the subinterval corresponds to a daily subinterval within the first time period.

25. The method of claim 23 wherein the second time period is the same as the subinterval.

26. The method of claim 23 further comprising:
providing a user interface through which a user can adjustably define a plurality of parameters for the sensor data;
defining the first time period and the subinterval in response to user input through the provided user interface.

27. The method of claim 26 wherein the providing step comprises providing the user interface in response to user input with respect to the alert.

28. The method of claim 2 wherein the health condition is representative of a physical and cognitive health condition of the person.

29. The method of claim 1, wherein the activity pattern frame of reference comprises (1) a statistical value about a daily total number of sensor hits during the first time period or (2) a statistical value about a daily total time for sensor firings during the first time period.

30. The method of claim 1, wherein the motion sensors comprise at least one motion sensor deployed in at least one of (1) a bathroom of the living unit, (2) a kitchen of the living unit, (3) a living room of the living unit, (4) a bedroom of the living unit, (5) a cup cabinet of the living unit, (6) an office of the living unit, (7) a bedroom of the living unit, (8) a plate cabinet of the living unit, (9) a shower of the living unit, (10) a closet of the living unit, (11) a silverware drawer of the living unit, (12) a den of the living unit, (13) a refrigerator of the living unit, (14) a front door of the living unit, and (15) a laundry of the living unit.

31. The method of claim 1, wherein the motion sensors comprise a plurality of motion sensors deployed in at least two of (1) a bathroom of the living unit, (2) a kitchen of the living unit, (3) a living room of the living unit, (4) a bedroom of the living unit, (5) a cup cabinet of the living unit, (6) an office of the living unit, (7) a bedroom of the living unit, (8) a plate cabinet of the living unit, (9) a shower of the living unit, (10) a closet of the living unit, (11) a silverware drawer of the living unit, (12) a den of the living unit, (13) a refrigerator of the living unit, (14) a front door of the living unit, and (15) a laundry of the living unit.

32. The method of claim 1, further comprising:
defining the first time period in response to user input.

33. A system comprising:
a plurality of motion sensors and a bed sensor deployed in a living unit; and
a computer system for communication with the motion sensors and the bed sensor, wherein the computer system is configured to:
process sensor data from the motion sensors and the bed sensor for a first time period to establish a frame of reference for an activity pattern by a person residing in the living unit, wherein the activity pattern frame of reference represents a health condition of a person residing in the living unit, wherein the processed sensor data for the first time period comprises a plurality of data values corresponding to a plurality of subintervals within the first time period, wherein each subinterval data value represents (1) a total number of sensor hits during that subinterval of the first time period or (2) a total time for sensor firings during that subinterval of the first time period, and wherein the activity pattern frame of reference comprises a statistical value about the subinterval data values over the first time period;

compute a standard deviation for the processed sensor data over the first time period based on the subinterval data values;

define a statistical parameter threshold, wherein the statistical parameter threshold comprises a defined number of the standard deviations;

process additional sensor data from the plurality of motion sensors and the bed sensor deployed in the living unit for a second time period, the second time period occurring after the first time period;

compute a value for the activity pattern for the second time period based on the processed additional sensor data, the computed activity pattern value of the second time period also representing a health condition of the person, wherein the computed activity pattern value comprises (1) data about a total number of sensor hits during the second time period if the activity pattern frame of reference is based on the total number of sensor hits during the first time period or (2) data about a total time for sensor firings during the second time period if the activity pattern frame of reference is based on the total time for sensor firings during the first time period;

compare the computed activity pattern value with the activity pattern frame of reference and the defined statistical parameter threshold to determine whether the computed activity pattern value deviates from the activity pattern frame of reference by more than the defined number of the standard deviations;

generate an alert based on a determination that the computed activity pattern value deviates from the activity pattern frame of reference by more than the defined number of standard deviations;

receive a feedback response to the alert, the feedback response including feedback regarding clinical relevance of the alert; and adjust the defined number of the standard deviations for the statistical parameter threshold to a different defined number of the standard deviations based on the feedback response to the alert.

34. The system of claim 33 wherein the computer system is further configured to provide a plurality of graphical user interfaces (GUIs) for presentation to a user, at least one of the GUIs configured to receive inputs from the user that define the first time period and the subinterval.

35. The system of claim 34 wherein at least another of the GUIs is configured to display sensor data over the defined first time period for each defined subinterval.

* * * * *